(12) United States Patent  (10) Patent No.: US 7,901,423 B2
Stulen et al.  (45) Date of Patent: Mar. 8, 2011

(54) FOLDED ULTRASONIC END EFFECTORS WITH INCREASED ACTIVE LENGTH

(75) Inventors: Foster B. Stulen, Mason, OH (US); Kevin L. Houser, Springboro, OH (US); Eitan T. Wiener, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 339 days.

(21) Appl. No.: 11/998,758

(22) Filed: Nov. 30, 2007

(65) Prior Publication Data

US 2009/0143796 A1  Jun. 4, 2009

(51) Int. Cl.
 *A61B 17/32* (2006.01)
(52) U.S. Cl. ........................................................ 606/169
(58) Field of Classification Search .............. 604/22; 606/37, 39, 40, 45, 49, 167, 169, 170, 171; 600/459, 461, 462, 463, 464; 601/2, 3; 73/290 V
See application file for complete search history.

(56) References Cited

U.S. PATENT DOCUMENTS

| | | | |
|---|---|---|---|
| 2,736,960 | A | 3/1956 | Armstrong |
| 2,849,788 | A | 9/1958 | Creek |
| 3,015,961 | A | 1/1962 | Roney |
| 3,526,219 | A | 9/1970 | Balamuth |
| 3,636,943 | A | 1/1972 | Balamuth |
| 3,776,238 | A | 12/1973 | Peyman et al. |
| 3,805,787 | A | 4/1974 | Banko |
| 3,862,630 | A | 1/1975 | Balamuth |
| 3,918,442 | A | 11/1975 | Nikolaev et al. |
| 3,956,826 | A | 5/1976 | Perdreaux, Jr. |
| 4,156,187 | A | 5/1979 | Murry et al. |
| 4,200,106 | A | 4/1980 | Douvas et al. |
| 4,445,063 | A | 4/1984 | Smith |
| 4,491,132 | A | 1/1985 | Aikins |
| 4,634,420 | A | 1/1987 | Spinosa et al. |
| 4,640,279 | A | 2/1987 | Beard |
| 4,708,127 | A | 11/1987 | Abdelghani |
| 4,832,683 | A | 5/1989 | Idemoto et al. |

(Continued)

FOREIGN PATENT DOCUMENTS

EP  0443256 A1  8/1991

(Continued)

OTHER PUBLICATIONS

Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).

(Continued)

*Primary Examiner* — Anhtuan T Nguyen
*Assistant Examiner* — Jonathan W Miles

(57) ABSTRACT

An end effector for use with an ultrasonic surgical instrument. A body extends along a longitudinal axis. The body includes a proximal end and a distal end. The proximal end of the body is configured to couple to an ultrasonic transducer configured to produce vibrations at a predetermined frequency. A folded element includes a first end coupled to the distal end of the body at a predetermined region between a node and an antinode. The folded element extends along the longitudinal axis from the distal end to the proximal end of the body. The folded element comprises a second free acoustic end. A distal portion of the body and the folded element define a parallel acoustic path.

17 Claims, 16 Drawing Sheets

U.S. PATENT DOCUMENTS

| | | |
|---|---|---|
| 4,838,853 A | 6/1989 | Parisi |
| 4,850,354 A | 7/1989 | McGurk-Burleson et al. |
| 4,865,159 A | 9/1989 | Jamison |
| 4,896,009 A | 1/1990 | Pawlowski |
| 4,981,756 A | 1/1991 | Rhandhawa |
| 5,026,387 A | 6/1991 | Thomas |
| 5,112,300 A | 5/1992 | Ureche |
| 5,123,903 A | 6/1992 | Quaid et al. |
| 5,162,044 A | 11/1992 | Gahn et al. |
| 5,167,725 A | 12/1992 | Clark et al. |
| D332,660 S | 1/1993 | Rawson et al. |
| 5,176,695 A | 1/1993 | Dulebohn |
| 5,213,569 A | 5/1993 | Davis |
| 5,221,282 A | 6/1993 | Wuchinich |
| 5,226,910 A | 7/1993 | Kajiyama et al. |
| 5,241,236 A | 8/1993 | Sasaki et al. |
| 5,257,988 A | 11/1993 | L'Esperance, Jr. |
| 5,261,922 A * | 11/1993 | Hood ............................ 606/167 |
| 5,263,957 A | 11/1993 | Davison |
| 5,282,800 A | 2/1994 | Foshee et al. |
| D347,474 S | 5/1994 | Olson |
| 5,322,055 A | 6/1994 | Davison et al. |
| 5,324,299 A | 6/1994 | Davison et al. |
| 5,346,502 A | 9/1994 | Estabrook et al. |
| 5,366,466 A | 11/1994 | Christian et al. |
| D354,564 S | 1/1995 | Medema |
| 5,411,481 A | 5/1995 | Allen et al. |
| 5,419,761 A | 5/1995 | Narayanan et al. |
| 5,421,829 A | 6/1995 | Olichney et al. |
| 5,449,370 A | 9/1995 | Vaitekunas |
| 5,486,162 A | 1/1996 | Brumbach |
| 5,500,216 A | 3/1996 | Julian et al. |
| 5,501,654 A | 3/1996 | Failla et al. |
| 5,505,693 A | 4/1996 | Mackool |
| 5,562,609 A | 10/1996 | Brumbach |
| 5,562,610 A | 10/1996 | Brumbach |
| 5,601,601 A | 2/1997 | Tal et al. |
| 5,607,436 A | 3/1997 | Pratt et al. |
| 5,618,492 A | 4/1997 | Auten et al. |
| 5,628,760 A | 5/1997 | Knoepfler |
| 5,630,420 A | 5/1997 | Vaitekunas |
| D381,077 S | 7/1997 | Hunt |
| 5,653,713 A | 8/1997 | Michelson |
| 5,669,922 A | 9/1997 | Hood |
| 5,674,235 A | 10/1997 | Parisi |
| 5,690,269 A | 11/1997 | Bolanos et al. |
| 5,694,936 A | 12/1997 | Fujimoto et al. |
| 5,713,896 A | 2/1998 | Nardella |
| 5,741,226 A | 4/1998 | Strukel et al. |
| 5,810,859 A | 9/1998 | DiMatteo et al. |
| 5,827,323 A | 10/1998 | Klieman et al. |
| 5,828,160 A | 10/1998 | Sugishita |
| 5,843,109 A | 12/1998 | Mehta et al. |
| 5,879,364 A | 3/1999 | Bromfield et al. |
| 5,893,835 A | 4/1999 | Witt et al. |
| 5,897,569 A | 4/1999 | Kellogg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,954,736 A | 9/1999 | Bishop et al. |
| 5,954,746 A | 9/1999 | Holthaus et al. |
| 5,957,943 A | 9/1999 | Vaitekunas |
| 5,968,007 A | 10/1999 | Simon et al. |
| 5,968,060 A | 10/1999 | Kellogg |
| D416,089 S | 11/1999 | Barton et al. |
| 5,989,274 A | 11/1999 | Davison et al. |
| 5,989,275 A | 11/1999 | Estabrook et al. |
| 6,033,375 A | 3/2000 | Brumbach |
| 6,063,098 A | 5/2000 | Houser et al. |
| 6,066,132 A | 5/2000 | Chen et al. |
| 6,068,647 A | 5/2000 | Witt et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,109,500 A | 8/2000 | Alli et al. |
| 6,113,594 A | 9/2000 | Savage |
| 6,139,320 A | 10/2000 | Hahn |
| 6,152,902 A | 11/2000 | Christian et al. |
| 6,159,160 A | 12/2000 | Hsei et al. |
| 6,159,175 A | 12/2000 | Strukel et al. |
| 6,206,844 B1 | 3/2001 | Reichel et al. |
| 6,210,403 B1 | 4/2001 | Klicek |
| 6,214,023 B1 | 4/2001 | Whipple et al. |
| 6,238,366 B1 | 5/2001 | Savage et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,267,761 B1 | 7/2001 | Ryan |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,283,981 B1 | 9/2001 | Beaupre |
| 6,309,400 B2 | 10/2001 | Beaupre |
| 6,319,221 B1 | 11/2001 | Savage et al. |
| 6,325,811 B1 | 12/2001 | Messerly |
| 6,328,751 B1 | 12/2001 | Beaupre |
| 6,352,532 B1 | 3/2002 | Kramer et al. |
| 6,383,194 B1 | 5/2002 | Pothula |
| 6,387,109 B1 | 5/2002 | Davison et al. |
| 6,391,042 B1 | 5/2002 | Cimino |
| 6,416,486 B1 | 7/2002 | Wampler |
| 6,423,073 B2 | 7/2002 | Bowman |
| 6,423,082 B1 | 7/2002 | Houser et al. |
| 6,432,118 B1 | 8/2002 | Messerly |
| 6,436,114 B1 | 8/2002 | Novak et al. |
| 6,436,115 B1 | 8/2002 | Beaupre |
| 6,443,969 B1 | 9/2002 | Novak et al. |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,485,490 B2 | 11/2002 | Wampler et al. |
| 6,491,708 B2 | 12/2002 | Madan et al. |
| 6,497,715 B2 | 12/2002 | Satou |
| 6,500,188 B2 | 12/2002 | Harper et al. |
| 6,524,316 B1 | 2/2003 | Nicholson et al. |
| 6,537,291 B2 | 3/2003 | Friedman et al. |
| 6,543,456 B2 | 4/2003 | Freeman |
| 6,544,260 B1 | 4/2003 | Markel et al. |
| 6,561,983 B2 | 5/2003 | Cronin et al. |
| 6,582,451 B1 | 6/2003 | Marucci et al. |
| 6,589,200 B1 | 7/2003 | Schwemberger et al. |
| 6,589,239 B2 | 7/2003 | Khandkar et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,662,127 B2 | 12/2003 | Wiener et al. |
| 6,663,941 B2 | 12/2003 | Brown et al. |
| 6,676,660 B2 | 1/2004 | Wampler et al. |
| 6,678,621 B2 | 1/2004 | Wiener et al. |
| 6,679,899 B2 | 1/2004 | Wiener et al. |
| 6,682,544 B2 | 1/2004 | Mastri et al. |
| 6,716,215 B1 | 4/2004 | David et al. |
| 6,733,506 B1 | 5/2004 | McDevitt et al. |
| 6,773,444 B2 | 8/2004 | Messerly |
| 6,786,383 B2 | 9/2004 | Stegelmann |
| 6,790,216 B1 | 9/2004 | Ishikawa |
| 6,869,439 B2 | 3/2005 | White et al. |
| 6,875,220 B2 | 4/2005 | Du et al. |
| 6,908,472 B2 | 6/2005 | Wiener et al. |
| 6,929,632 B2 | 8/2005 | Nita et al. |
| D509,589 S | 9/2005 | Wells |
| 6,945,981 B2 | 9/2005 | Donofrio et al. |
| D511,145 S | 11/2005 | Donofrio et al. |
| 6,976,969 B2 | 12/2005 | Messerly |
| 6,977,495 B2 | 12/2005 | Donofrio |
| 6,984,220 B2 | 1/2006 | Wuchinich |
| 7,041,088 B2 | 5/2006 | Nawrocki et al. |
| 7,074,219 B2 | 7/2006 | Levine et al. |
| 7,077,039 B2 | 7/2006 | Gass et al. |
| 7,077,853 B2 | 7/2006 | Kramer et al. |
| 7,108,695 B2 | 9/2006 | Witt et al. |
| 7,118,564 B2 | 10/2006 | Ritchie et al. |

| | | | | | | |
|---|---|---|---|---|---|---|
| 7,135,018 B2 | 11/2006 | Ryan et al. | | 2008/0058585 A1 | 3/2008 | Novak et al. |
| 7,135,030 B2 | 11/2006 | Schwemberger et al. | | 2008/0058775 A1 | 3/2008 | Darian et al. |
| 7,153,315 B2 | 12/2006 | Miller | | 2008/0058845 A1 | 3/2008 | Shimizu et al. |
| 7,156,189 B1 | 1/2007 | Bar-Cohen et al. | | 2008/0082039 A1 | 4/2008 | Babaev |
| 7,156,853 B2 | 1/2007 | Muratsu | | 2008/0177268 A1 | 7/2008 | Daum et al. |
| 7,157,058 B2 | 1/2007 | Marhasin et al. | | 2008/0188878 A1 | 8/2008 | Young |
| 7,159,750 B2 | 1/2007 | Racenet et al. | | 2008/0200940 A1 | 8/2008 | Eichmann et al. |
| 7,163,548 B2 | 1/2007 | Stulen et al. | | 2008/0208231 A1 | 8/2008 | Ota et al. |
| 7,179,271 B2 | 2/2007 | Friedman et al. | | 2008/0234708 A1 | 9/2008 | Houser et al. |
| 7,204,820 B2 | 4/2007 | Akahoshi | | 2008/0234709 A1 | 9/2008 | Houser |
| 7,223,229 B2 | 5/2007 | Inman et al. | | 2008/0234710 A1 | 9/2008 | Neurohr et al. |
| 7,229,455 B2 | 6/2007 | Sakurai et al. | | 2008/0234711 A1 | 9/2008 | Houser et al. |
| 7,273,483 B2 | 9/2007 | Wiener et al. | | 2008/0262490 A1 | 10/2008 | Williams |
| 7,331,410 B2 | 2/2008 | Yong et al. | | 2008/0287948 A1 | 11/2008 | Newton et al. |
| 7,380,695 B2 | 6/2008 | Doll et al. | | 2009/0030311 A1 | 1/2009 | Stulen et al. |
| 7,390,317 B2 | 6/2008 | Taylor et al. | | 2009/0030351 A1 | 1/2009 | Wiener et al. |
| D576,725 S | 9/2008 | Shumer et al. | | 2009/0030437 A1 | 1/2009 | Houser et al. |
| D578,643 S | 10/2008 | Shumer et al. | | 2009/0030438 A1 | 1/2009 | Stulen |
| D578,644 S | 10/2008 | Shumer et al. | | 2009/0030439 A1 | 1/2009 | Stulen |
| D578,645 S | 10/2008 | Shumer et al. | | 2009/0036911 A1 | 2/2009 | Stulen |
| 7,431,704 B2 | 10/2008 | Babaev | | 2009/0036912 A1 | 2/2009 | Wiener et al. |
| 7,472,815 B2 | 1/2009 | Shelton, IV et al. | | 2009/0036913 A1 | 2/2009 | Wiener et al. |
| 7,479,148 B2 | 1/2009 | Beaupre | | 2009/0036914 A1 | 2/2009 | Houser |
| 7,479,160 B2 | 1/2009 | Branch et al. | | 2009/0082716 A1 | 3/2009 | Akahoshi |
| 7,503,893 B2 | 3/2009 | Kucklick | | 2009/0105750 A1 | 4/2009 | Price et al. |
| 7,534,243 B1 | 5/2009 | Chin et al. | | 2009/0143795 A1 | 6/2009 | Robertson |
| D594,983 S | 6/2009 | Price et al. | | 2009/0143806 A1 | 6/2009 | Witt et al. |
| D618,797 S | 6/2010 | Price et al. | | 2010/0036405 A1 | 2/2010 | Giordano et al. |
| 7,770,774 B2 | 8/2010 | Mastri et al. | | 2010/0179577 A1 | 7/2010 | Houser |
| 2001/0025184 A1 | 9/2001 | Messerly | | 2010/0187283 A1 | 7/2010 | Crainich et al. |
| 2001/0039419 A1 | 11/2001 | Francischelli et al. | | | | |
| 2002/0019649 A1 | 2/2002 | Sikora et al. | | FOREIGN PATENT DOCUMENTS | | |
| 2002/0022836 A1 | 2/2002 | Goble et al. | | EP | 0456470 A1 | 11/1991 |
| 2002/0077550 A1 | 6/2002 | Rabiner et al. | | EP | 0482195 B1 | 4/1992 |
| 2002/0156493 A1 | 10/2002 | Houser et al. | | EP | 0612570 B1 | 6/1997 |
| 2003/0055443 A1 | 3/2003 | Spotnitz | | EP | 0908148 B1 | 1/2002 |
| 2003/0204199 A1 | 10/2003 | Novak et al. | | EP | 1199044 B1 | 12/2005 |
| 2003/0212332 A1 | 11/2003 | Fenton et al. | | EP | 1844720 A1 | 10/2007 |
| 2004/0030254 A1 | 2/2004 | Babaev | | EP | 1862133 A1 | 12/2007 |
| 2004/0047485 A1 | 3/2004 | Sherrit et al. | | EP | 1974771 A1 | 10/2008 |
| 2004/0092921 A1 | 5/2004 | Kadziauskas et al. | | EP | 1832259 B1 | 6/2009 |
| 2004/0097919 A1 | 5/2004 | Wellman et al. | | WO | WO 01/54590 A1 | 8/2001 |
| 2004/0097996 A1 | 5/2004 | Rabiner et al. | | WO | WO 2005/122917 A1 | 12/2005 |
| 2004/0199193 A1 | 10/2004 | Hayashi et al. | | WO | WO 2006/042210 A2 | 4/2006 |
| 2004/0204728 A1 | 10/2004 | Haefner | | WO | WO 2007/047531 A2 | 4/2007 |
| 2004/0260300 A1 | 12/2004 | Gorensek et al. | | WO | WO 2009/027065 A1 | 3/2009 |
| 2005/0049546 A1 | 3/2005 | Messerly et al. | | | | |
| 2005/0143769 A1 | 6/2005 | White et al. | | OTHER PUBLICATIONS | | |
| 2005/0165345 A1 | 7/2005 | Laufer et al. | | | | |
| 2005/0177184 A1 | 8/2005 | Easley | | | | |
| 2005/0192610 A1 | 9/2005 | Houser et al. | | | | |
| 2005/0209620 A1 | 9/2005 | Du et al. | | | | |
| 2005/0261581 A1 | 11/2005 | Hughes et al. | | | | |
| 2005/0261588 A1 | 11/2005 | Makin et al. | | | | |
| 2005/0288659 A1 | 12/2005 | Kimura et al. | | | | |
| 2006/0030797 A1 | 2/2006 | Zhou et al. | | | | |
| 2006/0063130 A1 | 3/2006 | Hayman et al. | | | | |
| 2006/0079878 A1 | 4/2006 | Houser | | | | |
| 2006/0084963 A1 | 4/2006 | Messerly | | | | |
| 2006/0190034 A1 | 8/2006 | Nishizawa et al. | | | | |
| 2006/0211943 A1 | 9/2006 | Beaupre | | | | |
| 2006/0235306 A1 | 10/2006 | Cotter et al. | | | | |
| 2006/0253050 A1 | 11/2006 | Yoshimine et al. | | | | |
| 2007/0016235 A1 | 1/2007 | Tanaka et al. | | | | |
| 2007/0016236 A1 | 1/2007 | Beaupre | | | | |
| 2007/0055228 A1 | 3/2007 | Berg et al. | | | | |
| 2007/0060915 A1 | 3/2007 | Kucklick | | | | |
| 2007/0130771 A1 | 6/2007 | Ehlert et al. | | | | |
| 2007/0131034 A1 | 6/2007 | Ehlert et al. | | | | |
| 2007/0149881 A1 | 6/2007 | Rabin | | | | |
| 2007/0162050 A1 | 7/2007 | Sartor | | | | |
| 2007/0185380 A1 | 8/2007 | Kucklick | | | | |
| 2007/0219481 A1 | 9/2007 | Babaev | | | | |
| 2007/0249941 A1 | 10/2007 | Salehi et al. | | | | |
| 2007/0265560 A1 | 11/2007 | Soltani et al. | | | | |
| 2007/0275348 A1 | 11/2007 | Lemon | | | | |
| 2007/0282335 A1 | 12/2007 | Young et al. | | | | |
| 2007/0287933 A1 | 12/2007 | Phan et al. | | | | |
| 2008/0009848 A1 | 1/2008 | Paraschiv et al. | | | | |

U.S. Appl. No. 12/245,158, filed Oct. 3, 2008.
U.S. Appl. No. 29/292,295, filed Oct. 5, 2007.
U.S. Appl. No. 11/998,543, filed Nov. 30, 2007.
U.S. Appl. No. 29/327,737, filed Nov. 12, 2008.
U.S. Appl. No. 12/274,884, filed Nov. 20, 2008.
International Search Report for PCT/US2008/083735, Feb. 10, 2009 (7 pages).
Technology Overview, printed from www.harmonicscalpel.com, Internet site, website accessed on Jun. 13, 2007, (3 pages).
AST Products, Inc., "Principles of Video Contact Angle Analysis," 20 pages, (date unknown).
Lim et al., "A Review of Mechanism Used in Laparoscopic Surgical Instruments," Mechanism and Machine Theory, vol. 38, pp. 1133-1147, (2003).
Sherrit, S. et al., Novel Horn Designs for Ultrasonic/Sonic Cleaning Welding, Soldering, Cutting and Drilling, Proc. SPIE Smart Structures Conference, vol. 4701, Paper No. 34, San Diego, CA, Mar. 2002.
AST Products, Inc., "Principles of Video Contact Angle Analysis," 20 pages, (2006).
U.S. Appl. No. 12/469,293, filed May 20, 2009.
U.S. Appl. No. 12/469,308, filed May 20, 2009.
U.S. Appl. No. 12/503,769, filed Jul. 15, 2009.
U.S. Appl. No. 12/503,770, filed Jul. 15, 2009.
U.S. Appl. No. 12/503,766, filed Jul. 15, 2009.
U.S. Appl. No. 12/490,906, filed Jun. 24, 2009.
U.S. Appl. No. 12/490,922, filed Jun. 24, 2009.
U.S. Appl. No. 12/490,933, filed Jun. 24, 2009.

U.S. Appl. No. 12/490,948, filed Jun. 24, 2009.
U.S. Appl. No. 12/703,860, filed Feb. 11, 2010.
U.S. Appl. No. 12/703,864, filed Feb. 11, 2010.
U.S. Appl. No. 12/703,866, filed Feb. 11, 2010.
U.S. Appl. No. 12/703,870, filed Feb. 11, 2010.
U.S. Appl. No. 12/703,875, filed Feb. 11, 2010.
U.S. Appl. No. 12/703,877, filed Feb. 11, 2010.
U.S. Appl. No. 12/703,879, filed Feb. 11, 2010.
U.S. Appl. No. 12/703,885, filed Feb. 11, 2010.
U.S. Appl. No. 12/703,893, filed Feb. 11, 2010.
U.S. Appl. No. 12/703,899, filed Feb. 11, 2010.
U.S. Appl. No. 12/732,702, filed Mar. 26, 2010.
International Preliminary Report on Patentability for PCT/US2008/083735, Jun. 10, 2010 (6 pages).

U.S. Appl. No. 29/361,917, filed May 17, 2010.
U.S. Appl. No. 12/896,351, filed Oct. 1, 2010.
U.S. Appl. No. 12/896,479, filed Oct. 1, 2010.
U.S. Appl. No. 12/896,360, filed Oct. 1, 2010.
U.S. Appl. No. 12/896,345, filed Oct. 1, 2010.
U.S. Appl. No. 12/896,384, filed Oct. 1, 2010.
U.S. Appl. No. 12/896,467, filed Oct. 1, 2010.
U.S. Appl. No. 12/896,451, filed Oct. 1, 2010.
U.S. Appl. No. 12/896,470, filed Oct. 1, 2010.
U.S. Appl. No. 12/896,411, filed Oct. 1, 2010.
U.S. Appl. No. 12/896,420, filed Oct. 1, 2010.

* cited by examiner

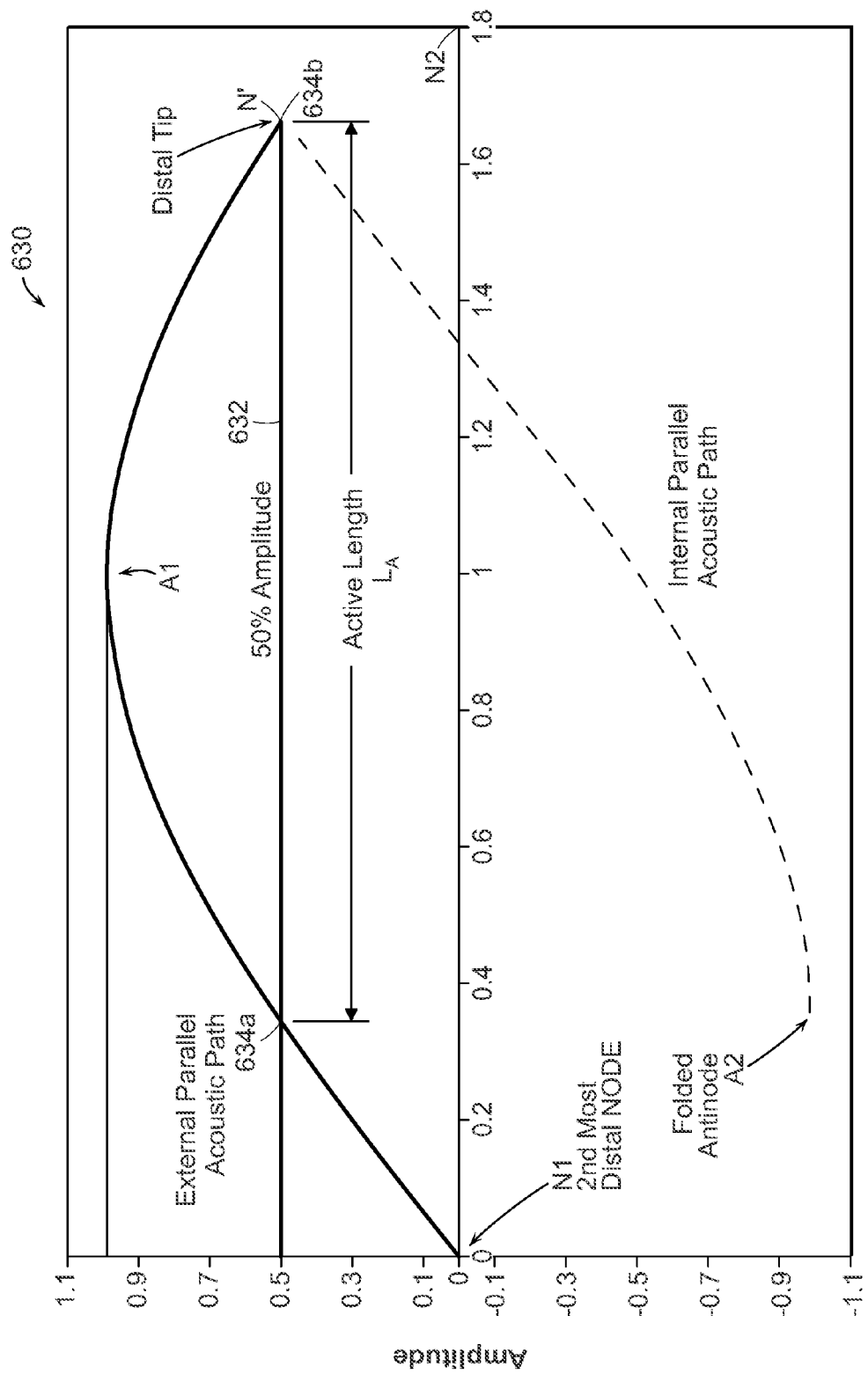

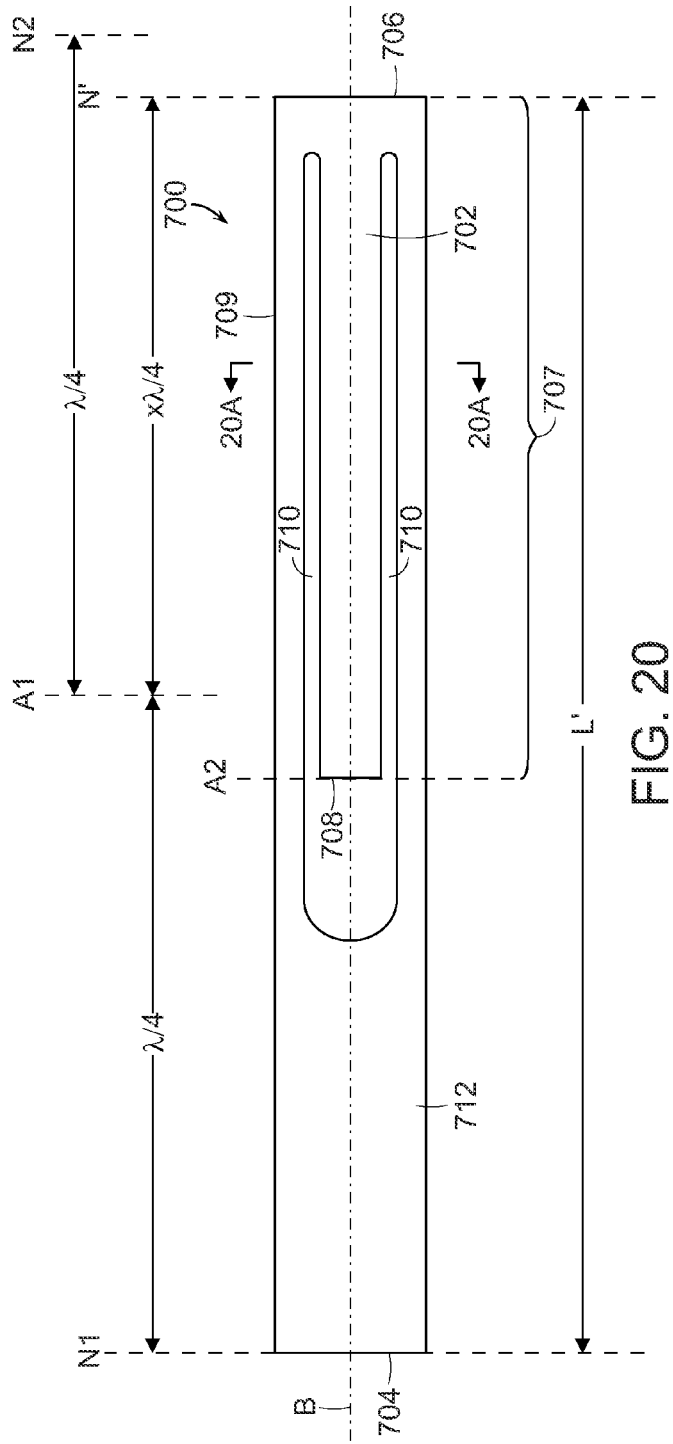
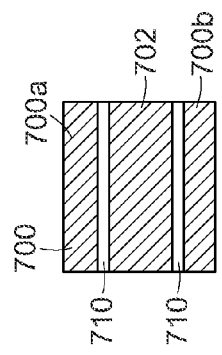
FIG. 20
FIG. 20A

US 7,901,423 B2

FOLDED ULTRASONIC END EFFECTORS WITH INCREASED ACTIVE LENGTH

BACKGROUND

Ultrasonic instruments, including both hollow core and solid core elements, are used for the safe and effective treatment of many medical conditions. Ultrasonic instruments, and particularly ultrasonic instruments comprising contact ultrasonic elements, are advantageous because they may be used to cut and/or coagulate tissue using energy in the form of mechanical vibrations transmitted to a surgical end effector at ultrasonic frequencies. Ultrasonic instruments utilizing contact ultrasonic elements are particularly advantageous because of the amount of ultrasonic energy that may be transmitted from an ultrasonic transducer, through a transmission component or waveguide, to the surgical end effector. Such instruments may be used for open or minimally invasive surgical procedures, such as endoscopic or laparoscopic surgical procedures, wherein the end effector is passed through a trocar to reach the surgical site.

Activating or exciting a single or multiple-element end effector of such instruments at ultrasonic frequencies induces longitudinal, transverse or torsional vibratory movement relative to the transmission component that generates localized heat within adjacent tissue, facilitating both cutting and coagulating. Because of the nature of ultrasonic instruments, a particular ultrasonically actuated end effector may be designed to perform numerous functions. Ultrasonic vibrations, when transmitted to organic tissue at suitable energy levels using a suitable end effector, may be used to cut, dissect, separate, lift, transect, elevate, coagulate or cauterize tissue, or to separate or scrape muscle tissue away from bone with or without the assistance of a clamping assembly.

Ultrasonic vibration is induced in the surgical end effector by electrically exciting a transducer, for example. The transducer may be constructed of one or more piezoelectric or magnetostrictive elements located in the instrument hand piece. Vibrations generated by the transducer section are transmitted to the surgical end effector via an ultrasonic transmission component such as a waveguide extending from the transducer section to the surgical end effector. The waveguide and end effector are most preferably designed to resonate at the same frequency as the transducer. Therefore, when an end effector is attached to a transducer the overall system frequency is the same frequency as the transducer itself.

The zero-to-peak amplitude of the longitudinal ultrasonic vibration at the tip, d, of the end effector behaves as a simple sinusoid at the resonant frequency as given by:

$$d = A(x)\sin(\omega t) \quad (1)$$

where:

$\omega$=the radian frequency which equals $2\pi$ times the cyclic frequency, f; and $A(x)$=the zero-to-peak amplitude as a function of position x along the blade.

The longitudinal excursion is defined as the peak-to-peak (p-t-p) amplitude, which is just twice the amplitude of the sine wave or 2A. $A(x)$ varies as a standing wave pattern and is referred to as the displacement curve. At displacement nodes, $A(x)$=zero and there is no ultrasonic excursion. At antinodes, $A(x)$ is at a local extreme, either a maximum or a minimum (minimum refers to a negative maximum).

Acoustic assemblies may comprise acoustic horns geometrically formed to amplify, attenuate, or transmit the amplitude of the vibrations produced by the piezoelectric or magnetostrictive actuators. Conventional horns generally have two distinct cross-sectional areas, usually with a taper between them, with the larger area, or input area, facing the actuation stack. Conventional horns are configured with a direct transition between the input and output areas. An amplifying acoustic horn (e.g., a fore-bell) is configured as a tapered solid with a larger diameter end (e.g., the input area) adapted to couple directly to the transducer and a smaller diameter end (e.g., the output area) at the tip adapted to couple to the end effector. The tapering cross-sectional area of the horn amplifies the limited displacements generated by the transducer. Vibration actuators operating from acoustic to ultrasonic frequencies generally include three main components. These components include the horn, a stack of piezoelectric or magnetostrictive elements (e.g., a transducer, actuator stack), and a backing material (e.g., an end-bell). The stack of piezoelectric elements is held in compression by a stress bolt that joins the backing material to the horn. The change in area is used to amplify the limited displacement that is induced by the stack.

Solid core ultrasonic instruments may be divided into single-element end effector devices and multiple-element end effector devices. Single-element end effector devices include instruments such as blades, scalpels, hooks, or ball coagulators. Multiple-element end effectors include the single-element end effector in conjunction with a mechanism to press or clamp tissue against the single-element end effector. Multiple-element end effectors comprise clamping scalpels, clamping coagulators or any combination of a clamping assembly with a single-element end effector generally referred to as clamp coagulators. Multiple-element end effectors may be employed when substantial pressure may be necessary to effectively couple ultrasonic energy to the tissue. Such end effectors apply a compressive or biasing force to the tissue to promote faster cutting and coagulation of the tissue, particularly loose and unsupported tissue.

Various design examples of vibration amplifiers, e.g., acoustic horns, are discussed in "Novel Horn Designs for Ultrasonic/Sonic Cleaning Welding, Soldering, Cutting and Drilling", Proc. SPIE Smart Structures Conference, Vol. 4701, Paper No. 34, San Diego, Calif., March 2002. Additional examples of horn designs are discussed in United States Patent Application Publication US20040047485A1, titled "Folded Horns for Vibration Actuator". The first reference discusses a folded horn connected to an ultrasonic transducer or actuator and the other end is in contact with the work piece (e.g., an ultrasonic blade or an ultrasonic transmission component or waveguide coupled to the blade). The "distal end" of the folded horn described in the reference, however, is not in contact with the work piece.

There is a need, however, for an end effector comprising one or more folded elements to reduce the overall length of an end effector while remaining in contact with the target tissue. There is also a need for an end effector comprising moveable folded elements. There is also a need for an end effector comprising a folded element located at the distal end that is located neither at a node nor an antinode and operates at an intermediate displacement amplitude.

SUMMARY

In one embodiment, an end effector for use with an ultrasonic surgical instrument comprising a body extending along a longitudinal axis. The body comprises a proximal end and a distal end. The proximal end of the body is configured to couple to an ultrasonic transducer configured to produce vibrations at a predetermined frequency. A folded element comprises a first end coupled to the distal end of the body at a predetermined region between a node and an antinode. The folded element extends along the longitudinal axis from the distal end to the proximal end of the body. The folded element comprises a second free acoustic end. A distal portion of the body and the folded element define a parallel acoustic path.

FIGURES

The novel features of the various embodiments are set forth with particularity in the appended claims. The various embodiments, however, both as to organization and methods of operation, together with advantages thereof, may best be understood by reference to the following description, taken in conjunction with the accompanying drawings as follows.

FIG. 1 illustrates one embodiment of an ultrasonic system comprising a single-element end effector.

FIGS. 2 A-D illustrate one embodiment of an ultrasonic system comprising a multi-element end effector.

Figure 4:
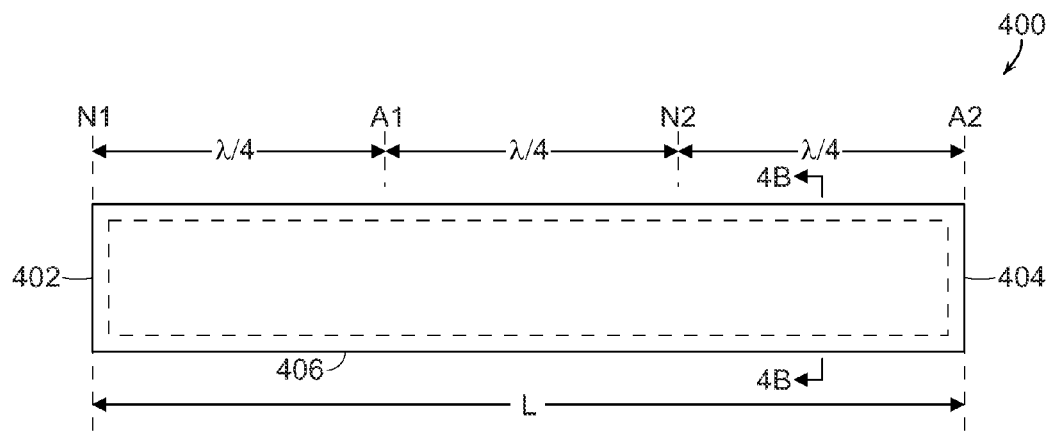
FIG. 4 is a schematic diagram of one embodiment of a hollow tubular end effector.
Figure 4A:
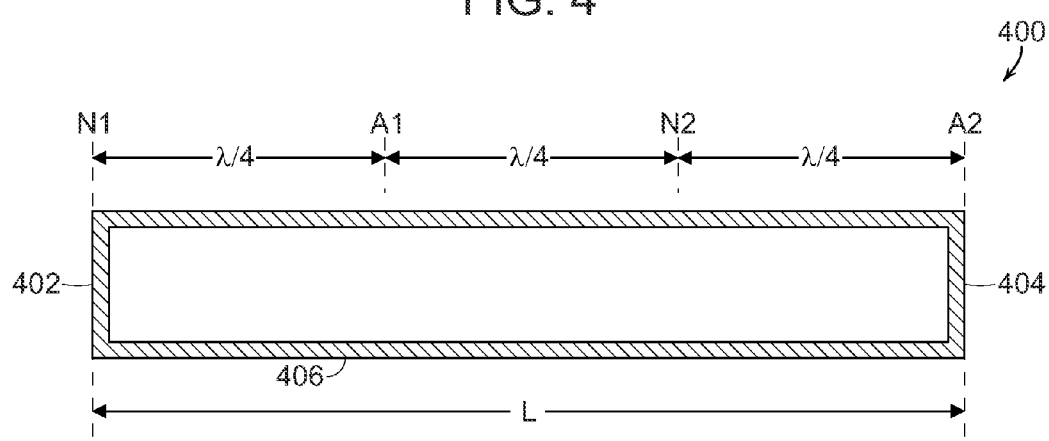
FIG. 4A is a longitudinal cross-sectional view of the end effector shown in FIG. 4.
Figure 4B:
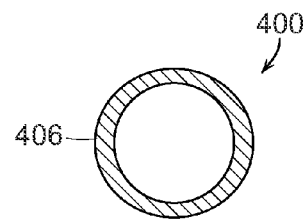
FIG. 4B is a cross-sectional view of the end effector shown in FIG. 4 taken along line 4B-4B.
Figure 7:
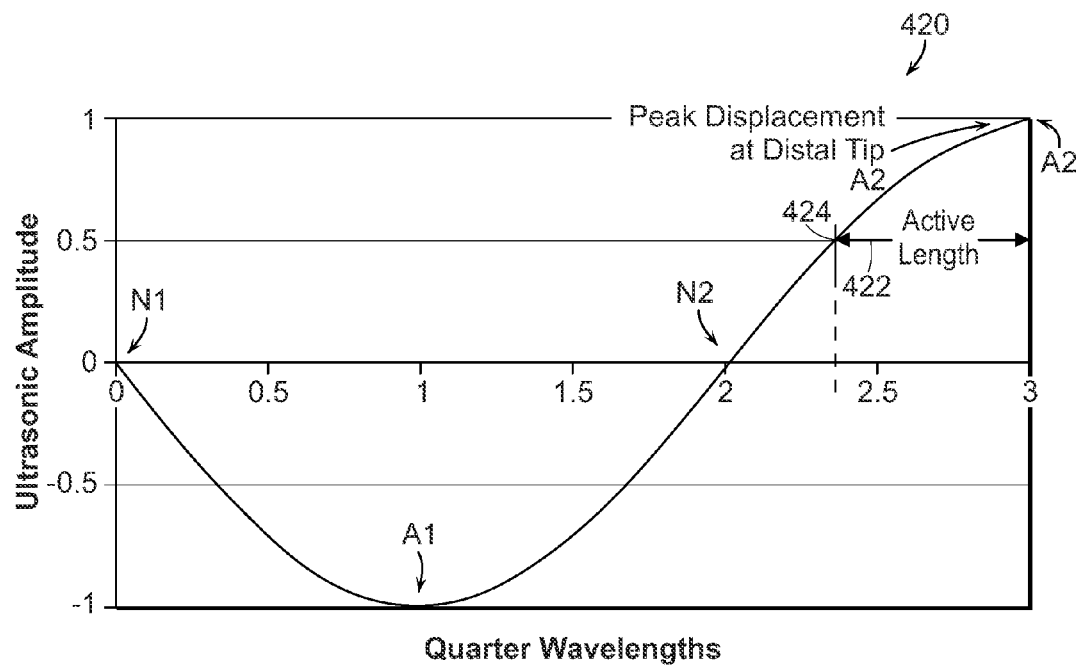

FIG. 7 graphically illustrates a characteristic ultrasonic displacement curve for an end effector shown in FIGS. 4, 4A, and 4B.

Figure 8:
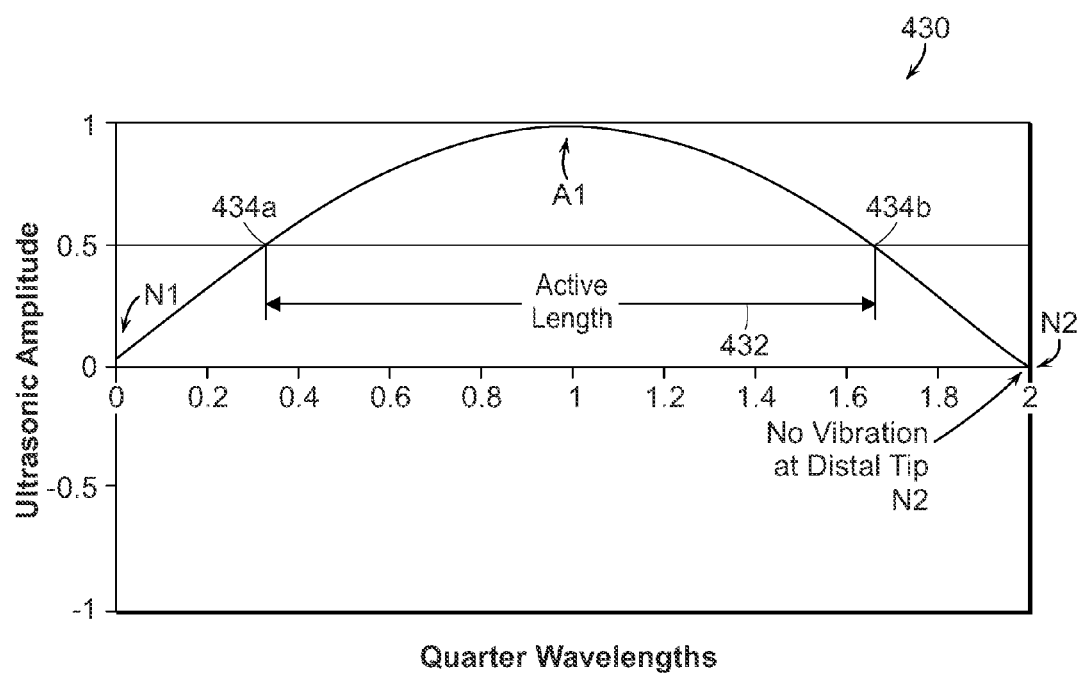

FIG. 8 graphically illustrates a characteristic ultrasonic displacement curve for the end effectors shown in FIGS. 5, 5A, and 5B FIGS. 6, 6A, 6B.

Figure 9:
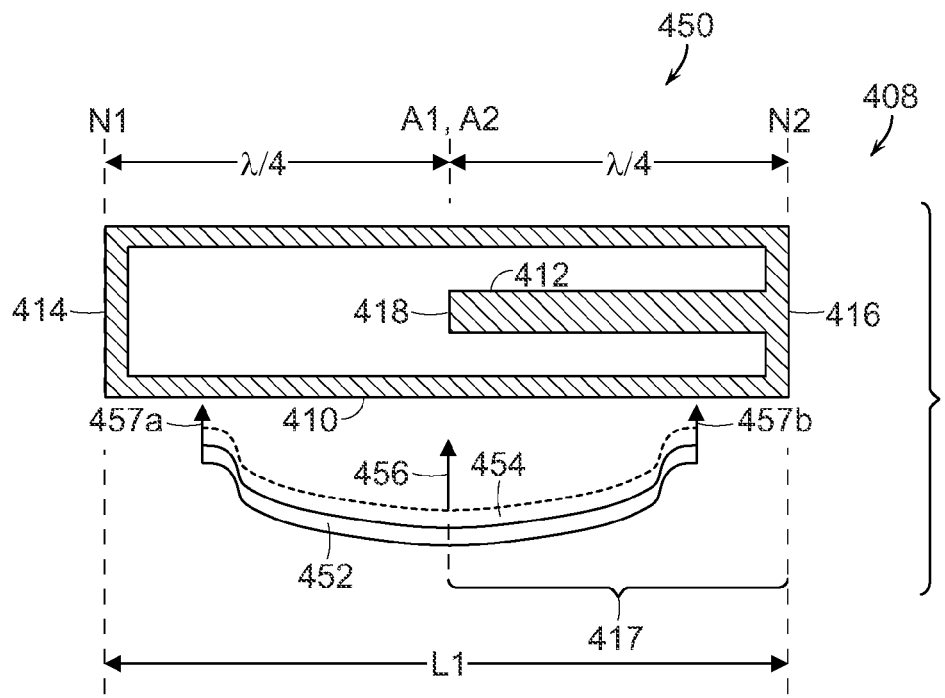

FIG. 9 illustrates a schematic diagram of one embodiment of a multi-element end effector comprising a folded element defining a parallel acoustic path.

Figure 10:
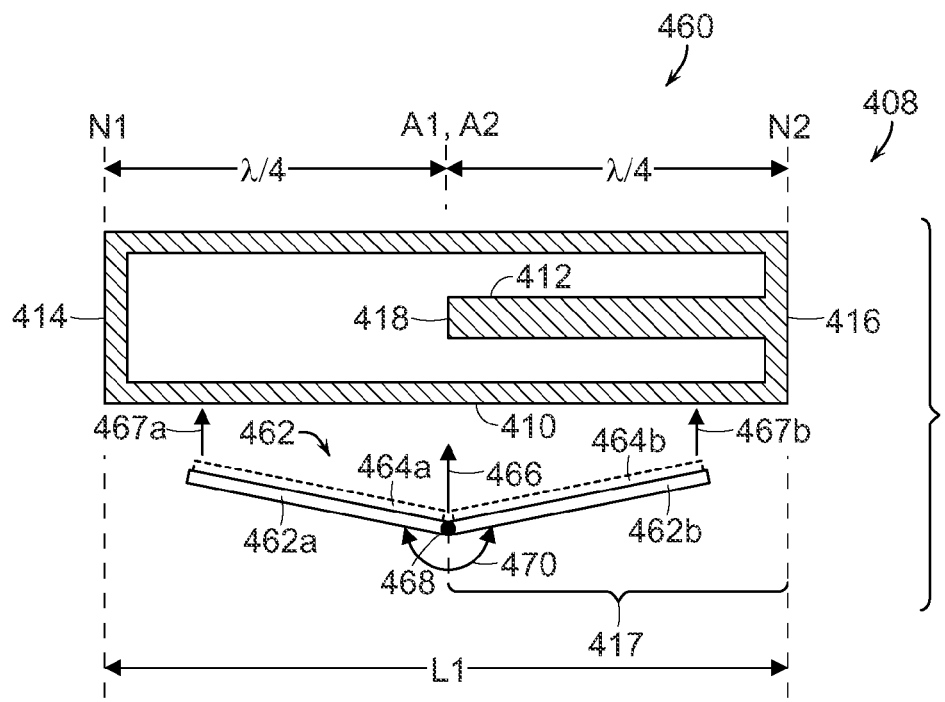

FIG. 10 illustrates a schematic diagram of one embodiment of a multi-element end effector comprising a folded element defining a parallel acoustic path.

Figure 11:
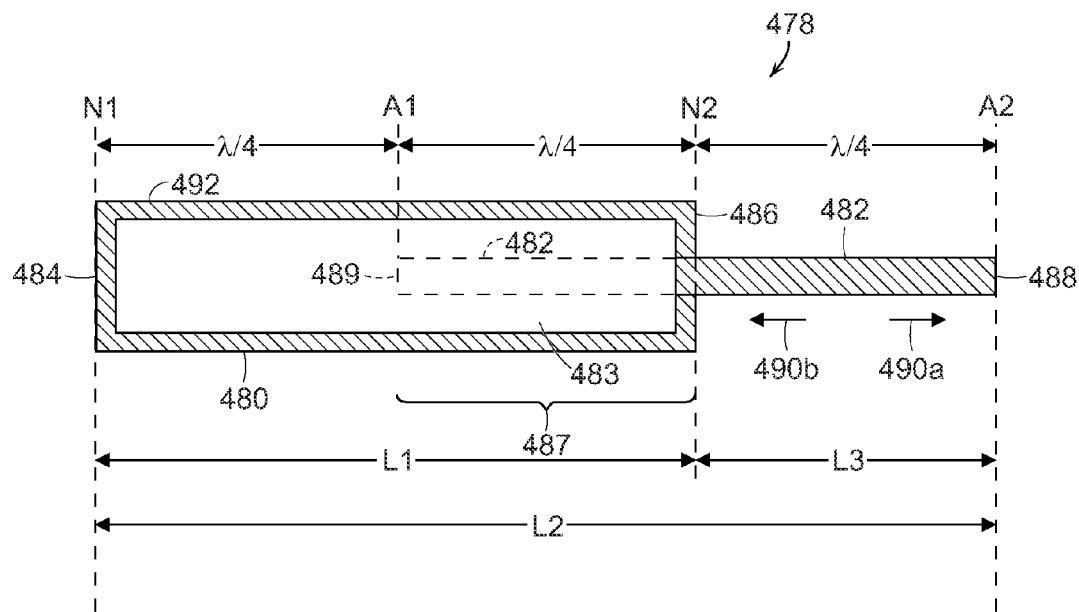

FIG. 11 illustrates a longitudinal cross-sectional view of one embodiment of an extendable tubular end effector.

Figure 12:
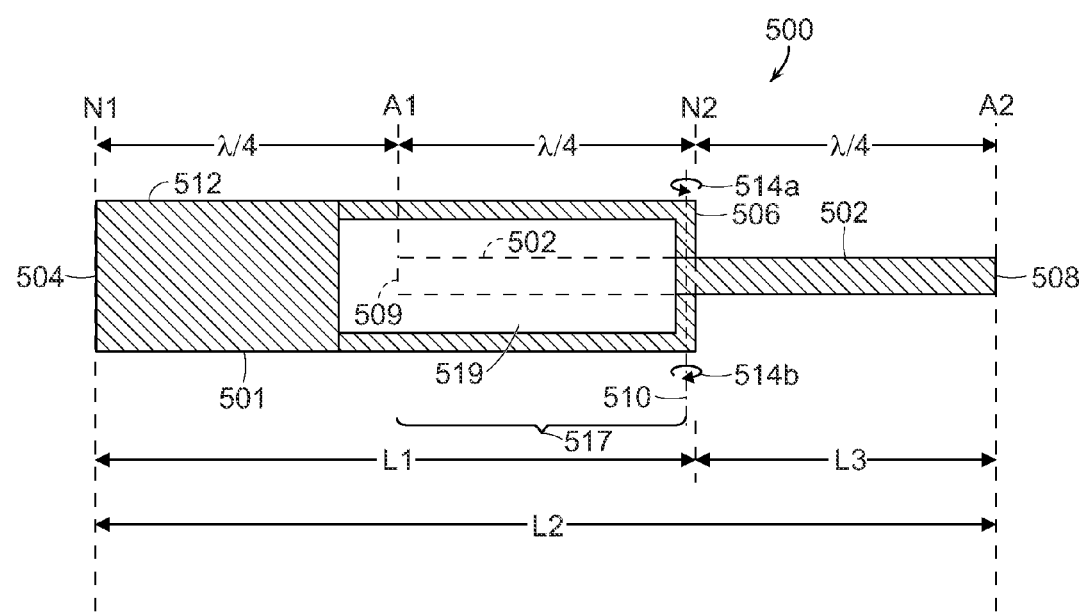

FIG. 12 illustrates a schematic diagram of one embodiment of a rotatable end effector.

Figure 13:
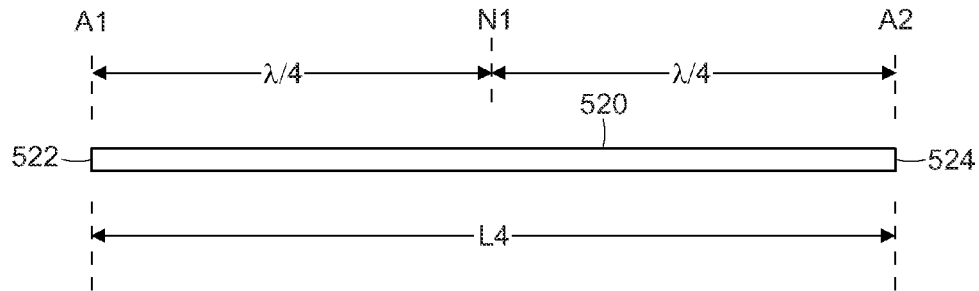

FIG. 13 is a schematic diagram of a straight elongated end effector.

Figure 14:
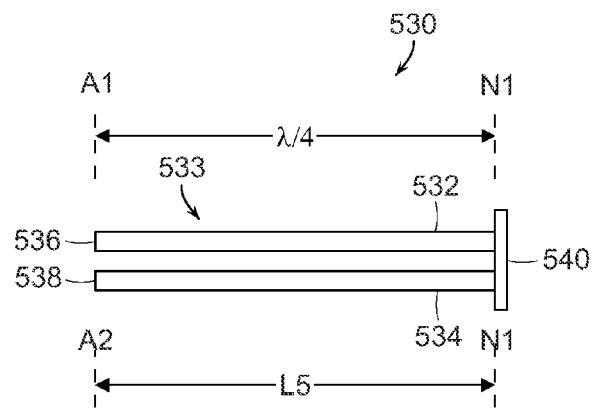

FIG. 14 is a schematic diagram of one embodiment of an effector comprising a folded element defining a parallel acoustic path.

Figure 15:
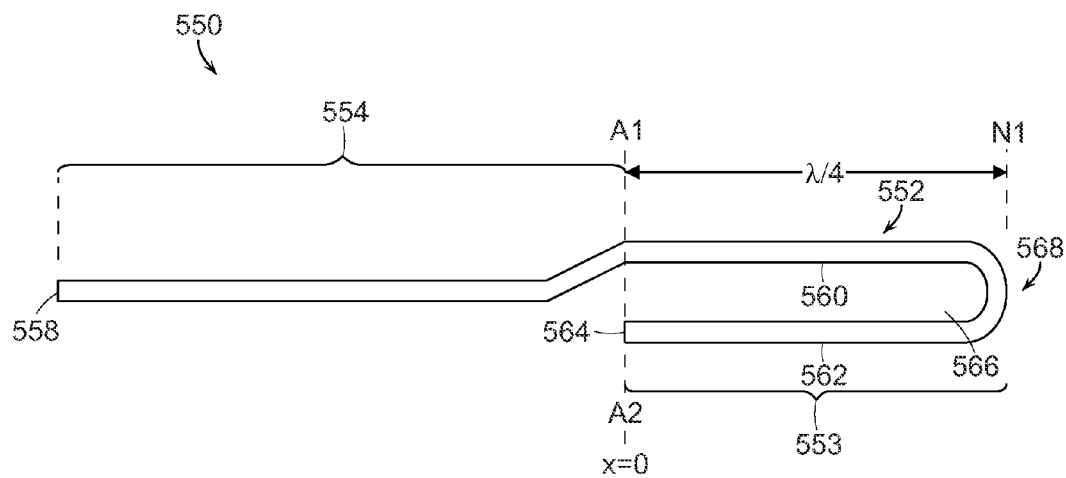

FIG. 15 is a schematic diagram of one embodiment of an end effector comprising a folded element defining a parallel acoustic path.

Figure 16:
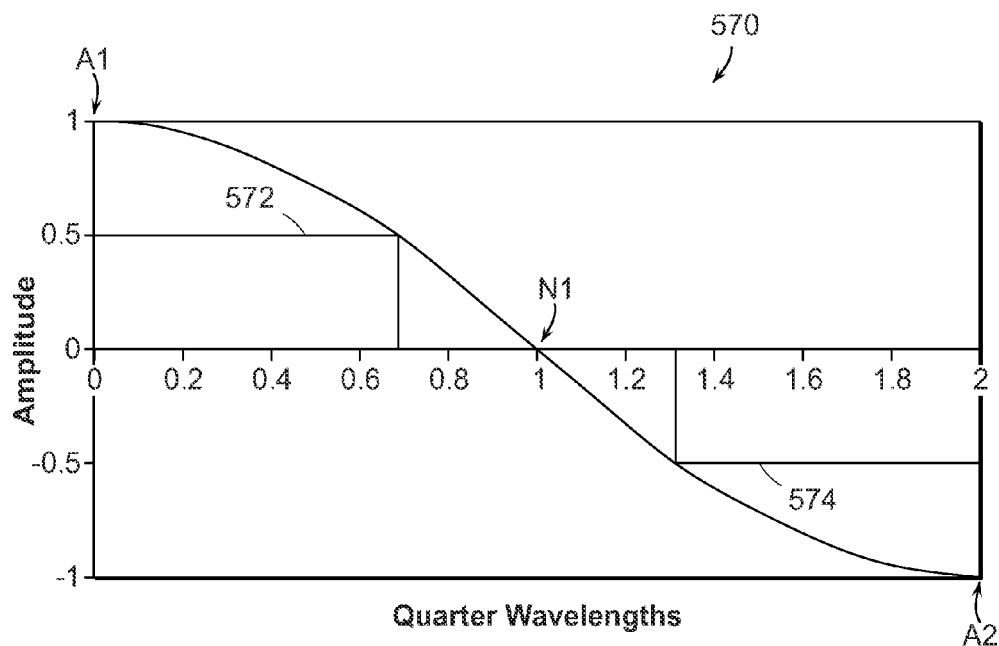

FIG. 16 graphically illustrates a characteristic ultrasonic displacement curve of the straight elongated end effector shown in FIG. 13.

Figure 17:
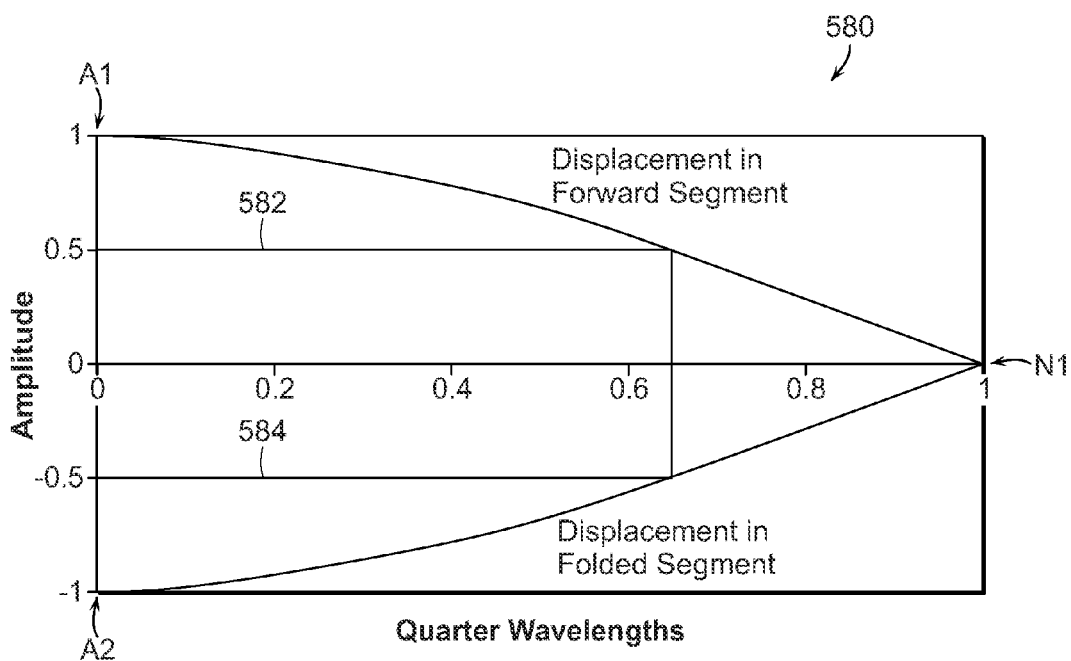

FIG. 17 graphically illustrates a characteristic ultrasonic displacement curve of one embodiment of an end effector comprising a folded element defining a parallel acoustic path shown in FIG. 14.

Figure 18:
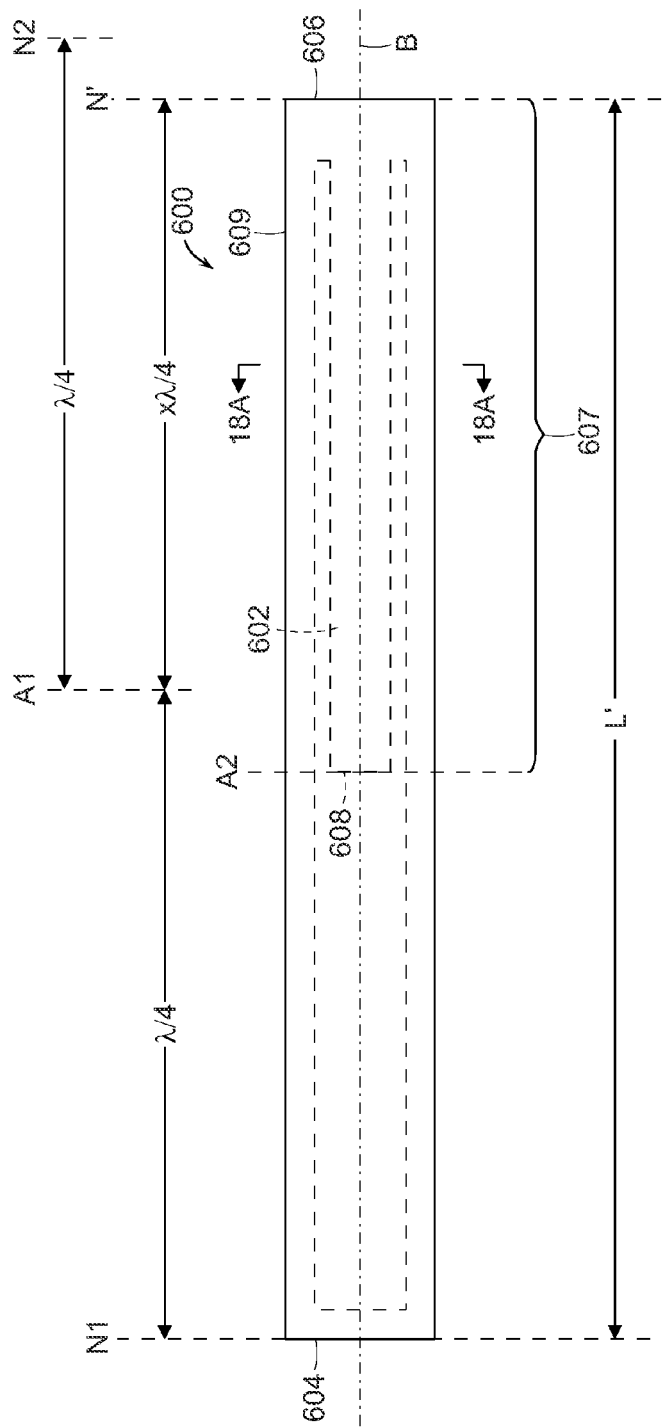

FIG. 18 is a schematic diagram of one embodiment of an end effector comprising a folded element defining a parallel acoustic path.

Figure 18A:
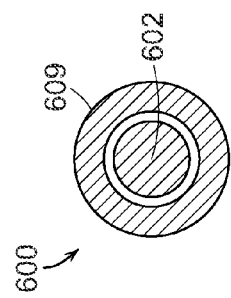

FIG. 18A is a cross-sectional view of the end effector shown in FIG. 18 taken along line 18A-18A.

FIG. 19 graphically illustrates a characteristic ultrasonic displacement curve of one embodiment of the end effector shown in FIGS. 18 and 18A comprising a folded element defining a parallel acoustic path.

FIG. 20 illustrates one embodiment of a slotted end effector comprising a folded element defining a parallel acoustic path.

FIG. 20A illustrates a cross-sectional view of the slotted end effector shown in FIG. 20 taken along line 20A-20A.

FIGS. 21A-D illustrate one embodiment of a multi-element slotted end effector comprising a folded element defining a parallel acoustic path.

DESCRIPTION

Before explaining the various embodiments in detail, it should be noted that the embodiments are not limited in their application or use to the details of construction and arrangement of parts illustrated in the context of the accompanying drawings and description. The illustrative embodiments may be implemented or incorporated in other embodiments, variations and modifications, and may be practiced or carried out in various ways. For example, the surgical instruments and end effector configurations disclosed below are illustrative only and not meant to limit the scope or application thereof. Furthermore, unless otherwise indicated, the terms and expressions employed herein have been chosen for the purpose of describing the illustrative embodiments for the convenience of the reader and are not limited in this context.

The various embodiments relate, in general, to ultrasonic surgical end effectors for use in surgical instruments and, more particularly, to ultrasonic surgical end effectors with improved elevating, cutting, and/or coagulation features, including, for example, improved bone and tissue removal, aspiration, and coagulation. An end effector may be straight, curved, hollow, or solid, and may be useful for either open or laparoscopic surgical procedures. An end effector according to the various embodiments described herein may be particularly useful in procedures where it is desirable to cut and coagulate soft tissue and control bleeding while simultaneously cutting tissue. An end effector according to various embodiments may be useful in surgical spine procedures, especially to assist in posterior access in removing muscle away from bone. An end effector according to the various embodiments described herein may reduce the amount of force required by the user to cut tissue or to separate muscle away from bone and, in various embodiments, may be useful to simultaneously hemostatically seal or cauterize the tissue. A variety of different end effector configurations are disclosed and described.

Examples of ultrasonic surgical instruments are disclosed in U.S. Pat. Nos. 5,322,055 and 5,954,736 and in combination with ultrasonic blades and surgical instruments disclosed in U.S. Pat. Nos. 6,309,400 B2, 6,278,218B1, 6,283,981 B1, and 6,325,811 B1, for example, are incorporated herein by reference in their entirety. These references disclose ultrasonic surgical instrument designs and blade designs where a longitudinal mode of the blade is excited. Certain embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and that the scope of the various embodiments is defined solely by the claims. The features illustrated or described in connection with one embodiment may be combined with the features of one or more other embodiments. Modifications and variations of the illustrated embodiments are intended to be included within the scope of the claims.

Ultrasonic instruments are designed and manufactured such that the maximum amplitude of the longitudinal ultrasonic vibration occurs at an antinode, which is localized at or near the distal end of the end effector to maximize the longitudinal excursion of the distal end. The minimum amplitude of the longitudinal ultrasonic vibration occurs at a node. The active length of an ultrasonic instrument may be defined as the distance from the distal end of the end effector (e.g., the location of the antinode where ultrasonic displacement is at a maximum) to a proximal location along the end effector prior to the adjacent node where the ultrasonic displacement decreases below a predetermined level of 50%, for example. A nodal gap is a length of an end effector segment surrounding a node where ultrasonic displacement is below the predetermined 50% level. Within the nodal gap, there is insufficient ultrasonic displacement to generate the necessary heat for efficient and/or effective cutting and/or coagulating of tissue.

The relatively low displacements in the vicinity of the node result in lower amounts of heat being delivered to tissue in contact with the end effector in a nodal gap region. In the nodal gap region, the tissue in contact with the end effector is not heated directly and is not effectively cut and/or coagulated. Accordingly, the tissue may stick to the end effector or may be desiccated without being transected. Thus, in ultrasonic surgical instruments, there may be advantageous to eliminating the nodal gap and/or increasing the active length of the end effector.

In conventional ultrasonic instruments, the active length of an end effector is generally less than a quarter wavelength ($\lambda/4$). A quarter wavelength is primarily determined by the frequency and speed of sound in the end effector material. The speed of sound in most metals suitable for ultrasonic components is approximately 5,000 meters per second. At 55.5 kHz the wavelength is approximately 3.58 inches, and a quarter wave is about 0.886 inches (in Ti6Al4V the quarter wavelength is 0.866 inches). The active length in titanium (Ti) is nominally 0.6 inches ($\approx$15 mm). While there are faster materials that provide longer active wavelengths, these materials are generally not suitable for surgical instruments.

Various embodiments of end effectors described herein comprise an active length that is longer than a quarter wavelength and may be an integral multiple of a quarter wavelength. The node (e.g., the location of minimum or no displacement) may be located at the distal end of the end effector that is presented to the patient. In such embodiments, the antinode (e.g., the location of maximum displacement) occurs somewhere along the longitudinal length of the end effector between a node and an antinode but not at the distal end. Moving away from the antinode, the displacement decreases to either side as the adjacent nodes are approached. The active length may be a multiple of the nominal active length.

As previously discussed, conventional ultrasonic instruments have a nominal active length that is limited to about 15 mm. In conventional designs, the active length is measured from the distal end (e.g., location of an antinode and maximum displacement) of the end effector to a location where the displacement amplitude falls to 50% of the maximum. Because the location generally occurs before the first distal node is reached, the active length of conventional end effectors is generally less than a quarter wavelength ($\lambda/4$).

In one embodiment, an ultrasonic instrument may comprise a single-element end effector (e.g., a blade) coupled to an acoustic waveguide or horn element. The end effector may comprise one or more "folded elements" as described in more detail below. The fold portion of the folded element may be located at or in proximity to a node, an antinode, or may be located anywhere therebetween. A folded element may be configured as a cutting and/or coagulating end effector with an active region located at and/or in between the fold and the distal end of the folded element. An end effector comprising a folded element according to the various embodiments discussed herein may comprise an active length that is longer than the active length of a conventional end effector without folded elements. The folded element also may comprise non-cutting "dull" regions, which may be located at a fold near the distal end of the instrument. In one embodiment, the fold may be located at or near a node. A fold located at a node remains a node, e.g., where ultrasonic displacement is zero, and provides a non-cutting "free-end" at the distal end of the end effector. The dull regions remain dull even when the end effector is ultrasonically activated. This may be desirable in certain medical procedures where the distal end of the end effector is not necessarily used for cutting tissue. In one embodiment, the fold may be located at or near an antinode. A fold located at or near an antinode remains an antinode, e.g., where ultrasonic displacement is maximum, and provides an active end for cutting and/or coagulating tissue that comes into contact therewith. In other embodiments, a fold may be located between a node and an antinode. The displacement at a fold located between a node and an antinode depends on whether the fold is located nearer to the node or the antinode. Accordingly, a desired displacement that is phased between zero and maximum may be realized by appropriately locating the fold between a node and antinode.

In another embodiment, an ultrasonic instrument may comprise a multi-element end effector (e.g., a blade and a clamping mechanism) coupled to an acoustic waveguide or horn element. The end effector may comprise one or more "folded elements". A clamp assembly is coupled to the end effector at a distal end as described in more detail below. The clamp assembly comprises a clamp arm and a single element end effector (e.g., a blade) to clamp tissue therebetween. As previously discussed, the fold may be located at or in proximity to a node, an antinode, or may be phased anywhere therebetween. The folded element may be configured to cut and/or coagulate. The active region may be located anywhere between the fold and the distal end of the end effector and may provide a longer active length than a conventional end effector without folded elements. Tissue may be received and squeezed between the end effector and a clamp arm. Pressure may be applied to the tissue located therebetween. In one embodiment, the clamp arm may be configured to apply minimum force at its longitudinal center where the displacement amplitude of the end effector is maximum and apply increasing force to either side of the center to compensate for the decreasing displacement amplitude along the active length on either side of the center. For example, the clamp arm may be configured to exert a normal minimum force at a point at or near the center of the clamp/arm assembly coinciding with an antinode of the end effector. The force applied by the clamp arm increases towards either end of the clamp arm. In this manner, the clamp arm exerts a force distribution profile over the active length of the end effector that is ideally inversely proportional to the velocity displacement amplitude of the end effector. Accordingly, the combination of the end effector velocity and the force exerted by the clamp arm on the end effector are substantially constant over the active length of the end effector.

In yet another embodiment, an ultrasonic instrument comprises an end effector may comprise one or more movable "folded elements". The folded element may be slideable, foldable, extendable, flappable, and/or rotatable. For example, an extendable folded element may be extended to provide a distal end that is selectable from an active cutting and/or coagulating mode, where the horn element is fully extended, to a dull mode where the horn element is fully retracted, or any mode therebetween where the horn element is located in an intermediate position between fully extended and fully retracted. A fully retracted folded element presents a dull or minimally active distal end that does not affect tissue in contact therewith. A fully extended folded element presents a maximally active distal end to the affect the tissue in contact therewith. A partially extended folded element presents a partially active distal end to the tissue in contact therewith.

In still another embodiment, an ultrasonic instrument comprises an end effector coupled to an acoustic waveguide or horn element. The end effector may comprise one or more "folded elements". The folded element may be formed as a hook at a distal end of the end effector. The folded element may be formed at or near a node, an antinode, or therebetween. In one embodiment, the hook may be formed by folding a distal segment of the end effector at a displacement node. In this configuration the distal end is free and remains a node, e.g., the ultrasonic displacement is minimal or approximately zero. The tip of the folded segment, however, remains an antinode where ultrasonic displacement is at a maximum. Tissue located within the hook may be continuously cut and/or coagulated. The operation of the hook shaped folded element is described in more detail below.

The various embodiments of the ultrasonic instruments described above may be driven by a conventional transducer configured to produce vibrations along a longitudinal axis of an ultrasonic transmission waveguide at a predetermined frequency. The end effector comprising the folded elements (folded element) may be coupled to the transducer via the waveguide or in direct contact in any suitable manner. The end effector may comprise a folded element and may be coupled to or form a portion of a waveguide extending along the longitudinal axis coupled to the transducer. The end effector includes a body comprising a folded element having a proximal end and a distal end. The folded element is movable along the longitudinal axis by the vibrations produced by the transducer.

Figure 1:
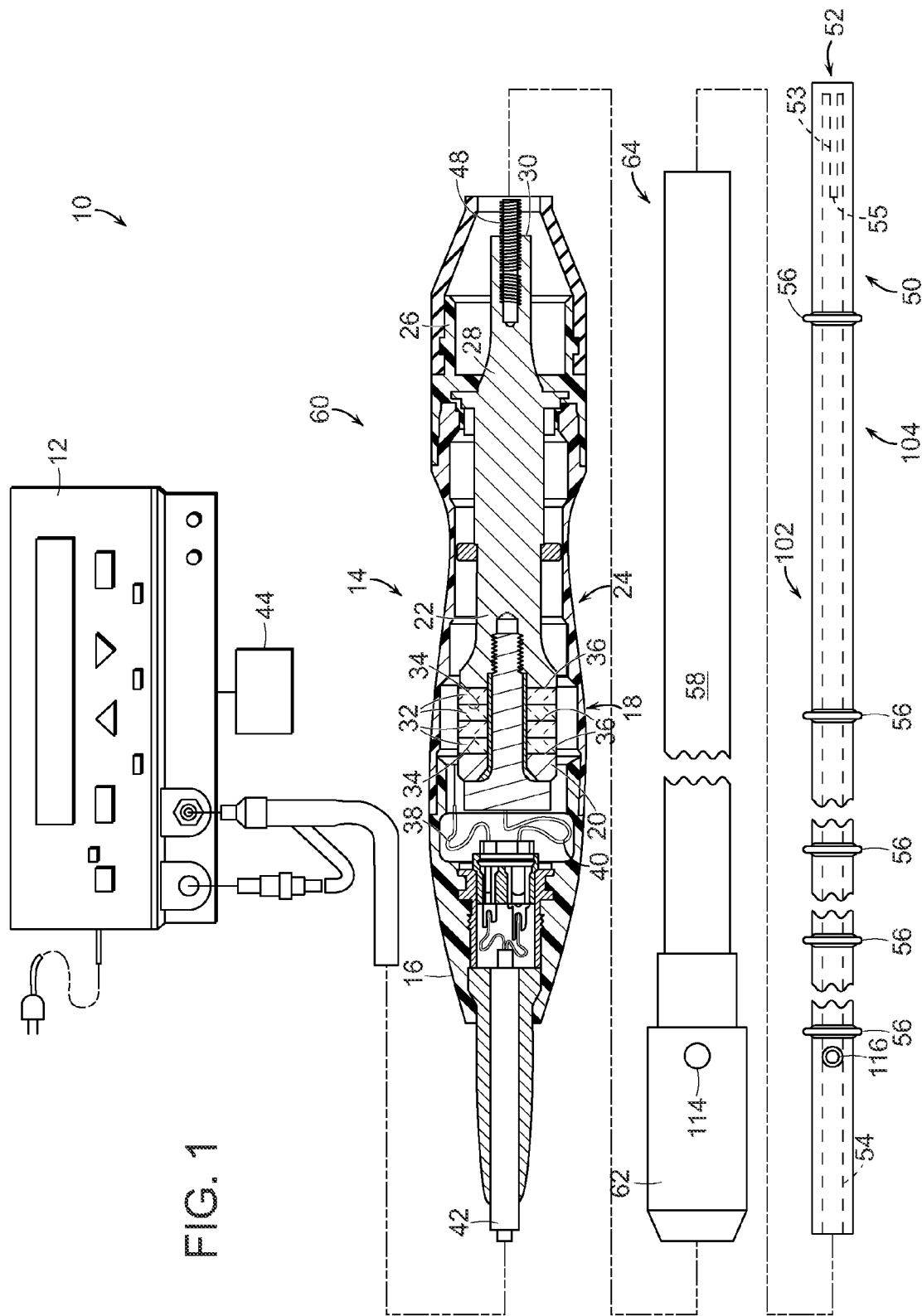

FIG. 1 illustrates one embodiment of an ultrasonic system 10 comprising a single-element end effector. One embodiment of the ultrasonic system 10 comprises an ultrasonic signal generator 12 coupled to an ultrasonic transducer 14, a hand piece assembly 60 comprising a hand piece housing 16, and an ultrasonically actuatable single-element end effector 50 shown as an ultrasonically actuatable blade comprising a folded element 53. The ultrasonic transducer 14, which is known as a "Langevin stack", generally includes a transduction portion 18, a first resonator portion or end-bell 20, and a second resonator portion or fore-bell 22, and ancillary components. The total construction of these components is a resonator. The ultrasonic transducer 14 is preferably an integral number of one-half system wavelengths ($n\lambda/2$; where "n" is any positive integer; e.g., n=1, 2, 3 . . . ) in length as will be described in more detail herein. An acoustic assembly 24 includes the ultrasonic transducer 14, a nose cone 26, a velocity transformer 28, and a surface 30.

It will be appreciated that the terms "proximal" and "distal" are used herein with reference to a clinician gripping the hand piece assembly 60. Thus, the end effector is distal with respect to the more proximal hand piece assembly 60. It will be further appreciated that, for convenience and clarity, spatial terms such as "top" and "bottom" also are used herein with respect to the clinician gripping the hand piece assembly 60. However, surgical instruments are used in many orientations and positions, and these terms are not intended to be limiting and absolute.

The distal end of the end-bell 20 is connected to the proximal end of the transduction portion 18, and the proximal end of the fore-bell 22 is connected to the distal end of the transduction portion 18. The fore-bell 22 and the end-bell 20 have a physical length determined by a number of variables, including the thickness of the transduction portion 18, the density and modulus of elasticity of the material used to manufacture the end-bell 20 and the fore-bell 22, and the resonant frequency of the ultrasonic transducer 14. The fore-bell 22 may be tapered inwardly from its proximal end to its distal end to amplify the ultrasonic vibration amplitude as the velocity transformer 28, or alternately may have no amplification. A suitable vibrational frequency range may be about 20 Hz to 120 kHz and a well-suited vibrational frequency range may be about 30-100 kHz. A suitable operational vibrational frequency may be approximately 55.5 kHz, for example. The second resonator portion or the fore-bell 22 may be folded to reduce the overall physical length of the fore-bell 22 while maintaining or increasing the acoustic length.

Piezoelectric elements 32 may be fabricated from any suitable material, such as, for example, lead zirconate-titanate, lead meta-niobate, lead titanate, barium titanate, or other piezoelectric ceramic material. Each of positive electrodes 34, negative electrodes 36, and the piezoelectric elements 32 has a bore extending through the center. The positive and negative electrodes 34 and 36 are electrically coupled to wires 38 and 40, respectively. The wires 38 and 40 are encased within a cable 42 and electrically connectable to the ultrasonic signal generator 12 of the ultrasonic system 10.

The ultrasonic transducer 14 of the acoustic assembly 24 converts the electrical signal from the ultrasonic signal generator 12 into mechanical energy that results in primarily a standing acoustic wave of longitudinal vibratory motion of the ultrasonic transducer 14 and the end effector 50 at ultrasonic frequencies. In another embodiment, the vibratory motion of the ultrasonic transducer may act in a different direction. For example, the vibratory motion may comprise a local longitudinal component of a more complicated motion of the tip of the ultrasonic system 10. A suitable generator is available as model number GEN04, from Ethicon Endo-Surgery, Inc., Cincinnati, Ohio. When the acoustic assembly 24 is energized, a vibratory motion standing wave is generated through the acoustic assembly 24. The ultrasonic system 10 is designed to operate at a resonance such that an acoustic standing wave pattern of predetermined amplitude is produced. The amplitude of the vibratory motion at any point along the acoustic assembly 24 depends upon the location along the acoustic assembly 24 at which the vibratory motion is measured. A zero crossing in the vibratory motion standing wave is generally referred to as a node (i.e., where motion is zero), and a local absolute value maximum or peak in the standing wave is generally referred to as an antinode (i.e., where local motion is maximal). The distance between an antinode and its nearest node is one quarter wavelength ($\lambda/4$).

The wires 38 and 40 transmit an electrical signal from the ultrasonic signal generator 12 to the positive electrodes 34 and the negative electrodes 36. The piezoelectric elements 32 are energized by the electrical signal supplied from the ultrasonic signal generator 12 in response to an actuator 44, such as a foot switch, for example, to produce an acoustic standing wave in the acoustic assembly 24. The alternating electrical signal causes the piezoelectric elements 32 to expand and contract in a continuous manner along the axis of the voltage gradient, producing longitudinal waves of ultrasonic energy. The expansion and contraction produce small displacements alternating in direction resulting in large alternating compression and tension forces within the material. An ultrasonic transmission assembly 102 includes the single-element end effector 50 coupled to an ultrasonic transmission waveguide 104. The ultrasonic energy is transmitted through the acoustic assembly 24 to the end effector 50 via a transmission component such as the ultrasonic transmission waveguide 104. The ultrasonic transmission waveguide 104 may be preferably fabricated from a hollow core shaft constructed out of material that propagates ultrasonic energy efficiently, such as titanium alloy (i.e., Ti6Al4V) or an aluminum alloy, for example. In other embodiments, the ultrasonic transmission waveguide 104 may be formed as a solid core transmission waveguide.

In order for the acoustic assembly 24 to deliver energy to the single-element end effector 50, all components of the acoustic assembly 24 are acoustically coupled to the end effector 50. The distal end of the ultrasonic transducer 14 may be acoustically coupled at the surface 30 to the proximal end of the ultrasonic transmission waveguide 104 by a threaded connection such as a stud 48.

The components of the acoustic assembly 24 are preferably acoustically tuned such that the length of any assembly is an integral number of one-half wavelengths ($n\lambda/2$), where the wavelength $\lambda$ is the wavelength of a pre-selected or operating longitudinal vibration drive frequency $f_d$ of the acoustic assembly 24. It is also contemplated that the acoustic assembly 24 may incorporate any suitable arrangement of acoustic elements.

The end effector 50 may have a length substantially equal to an integral multiple of one-half system wavelengths ($n\lambda/2$). The blade comprises a distal end 52, which coincides with the physical distal end of the folded element 53. The folded element 53 comprises an acoustic distal end 55 located at an antinode in terms of displacement. The acoustic distal end 55 is located at a point of maximum amplitude of the longitudinal ultrasonic vibration and the ultrasonic displacement is at a maximum. In one embodiment, the distal end 52 of the end effector 50 coincides with the distal end of the folded element 53 and may be disposed near an antinode to provide the maximum longitudinal excursion of the distal end 52. The corresponding proximal end 55 of the folded element 53 may be disposed near a node. In another embodiment, the distal end 52 of the end effector 50 coincides with the distal end of the folded element 53 and may be disposed near a node to provide the minimum longitudinal excursion of the distal end 52. The corresponding proximal end 55 of the folded element 53 may be disposed near an antinode to provide the maximum longitudinal excursion of the proximal end 55 of the folded element 53. In other embodiments, the distal end 52 of the end effector 50 coincides with the distal end of the folded element 53 and may be disposed between a node and an antinode to phase the longitudinal excursion of the distal end 52 accordingly. In the illustrated embodiment, the distal end 52 of the blade 50 coincides with the distal end of the folded element 53 and is disposed near a node to provide the minimum longitudinal excursion of the distal end 52. The corresponding proximal end 55 of the folded element 53 is disposed near an antinode to provide the maximum longitudinal excursion of the proximal end 55 of the folded element 53. When the transducer assembly is energized, the proximal end 55 of the folded element 53 may be configured to move in the range of, for example, approximately 10 to 500 microns peak-to-peak, and preferably in the range of about 30 to 150 microns at a predetermined vibrational frequency of 55 kHz, for example.

The end effector 50 may be coupled to the ultrasonic transmission waveguide 104. The blade 50 and the ultrasonic transmission waveguide 104 as illustrated are formed as a single unit construction from a material suitable for transmission of ultrasonic energy. Examples of such materials include Ti6Al4V (an alloy of Titanium including Aluminum and Vanadium), Aluminum, Stainless Steel, or other suitable materials. Alternately, the end effector 50 may be separable (and of differing composition) from the ultrasonic transmission waveguide 104, and coupled by, for example, a stud, weld, glue, quick connect, or other suitable known methods. The length of the ultrasonic transmission waveguide 104 may be substantially equal to an integral number of one-half wavelengths ($n\lambda/2$), for example. The ultrasonic transmission waveguide 104 may be preferably fabricated from a solid core shaft constructed out of material suitable to propagate ultrasonic energy efficiently, such as the titanium alloy discussed above (i.e., Ti6Al4V) or any suitable aluminum alloy, or other alloys, for example.

The ultrasonic transmission waveguide 104 comprises a longitudinally projecting attachment post 54 at a proximal end to couple to the surface 30 of the ultrasonic transmission waveguide 104 by a threaded connection such as the stud 48. In the embodiment illustrated in FIG. 1, the ultrasonic transmission waveguide 104 includes a plurality of stabilizing silicone rings or compliant supports 56 positioned at a plurality of nodes. The silicone rings 56 dampen undesirable vibration and isolate the ultrasonic energy from an outer sheath 58 ensuring the flow of ultrasonic energy in a longitudinal direction to the distal end 52 of the end effector 50 with maximum efficiency.

As shown in FIG. 1, the outer sheath 58 protects a user of the ultrasonic surgical instrument 10 and a patient from the ultrasonic vibrations of the ultrasonic transmission waveguide 104. The sheath 58 generally includes a hub 62 and an elongated tubular member 64. The tubular member 64 is attached to the hub 62 and has an opening extending longitudinally therethrough. The sheath 58 is threaded onto the distal end of the velocity transformer 28. The ultrasonic transmission waveguide 104 extends through the opening of the tubular member 64 and the silicone rings 56 isolate the ultrasonic transmission waveguide 104 from the outer sheath 58. The outer sheath 58 may be attached to the waveguide 104 with an isolator pin 114. The hole 116 in the waveguide 104 may occur nominally at a displacement node. The waveguide 104 may screw or snap onto the hand piece assembly 60 by the stud 48. The flat portions on the hub 62 may allow the assembly to be torqued to a required level.

The hub 62 of the sheath 58 is preferably constructed from plastic and the tubular member 64 is fabricated from stainless steel. Alternatively, the ultrasonic transmission waveguide 104 may incorporate a polymeric material surrounding it to isolate it from outside contact.

The distal end of the ultrasonic transmission waveguide 104 may be coupled to the proximal end of the single-element end effector 50 by an internal threaded connection, preferably at or near an antinode. It is contemplated that the end effector 50 may be attached to the ultrasonic transmission waveguide 104 by any suitable means, such as a welded joint or the like. Although the end effector 50 may be detachable from the ultrasonic transmission waveguide 104, it is also contemplated that the end effector 50 and the ultrasonic transmission waveguide 104 may be formed as a single unitary piece. In the illustrated embodiment, the ultrasonic waveguide 104 is implemented as an elongated transmission component and the end effector is implemented as a single-element end effector or the end effector 50 suitable to cut and/or coagulate tissue. The end effector 50 may be symmetrical or asymmetrical.

Figure 2A:
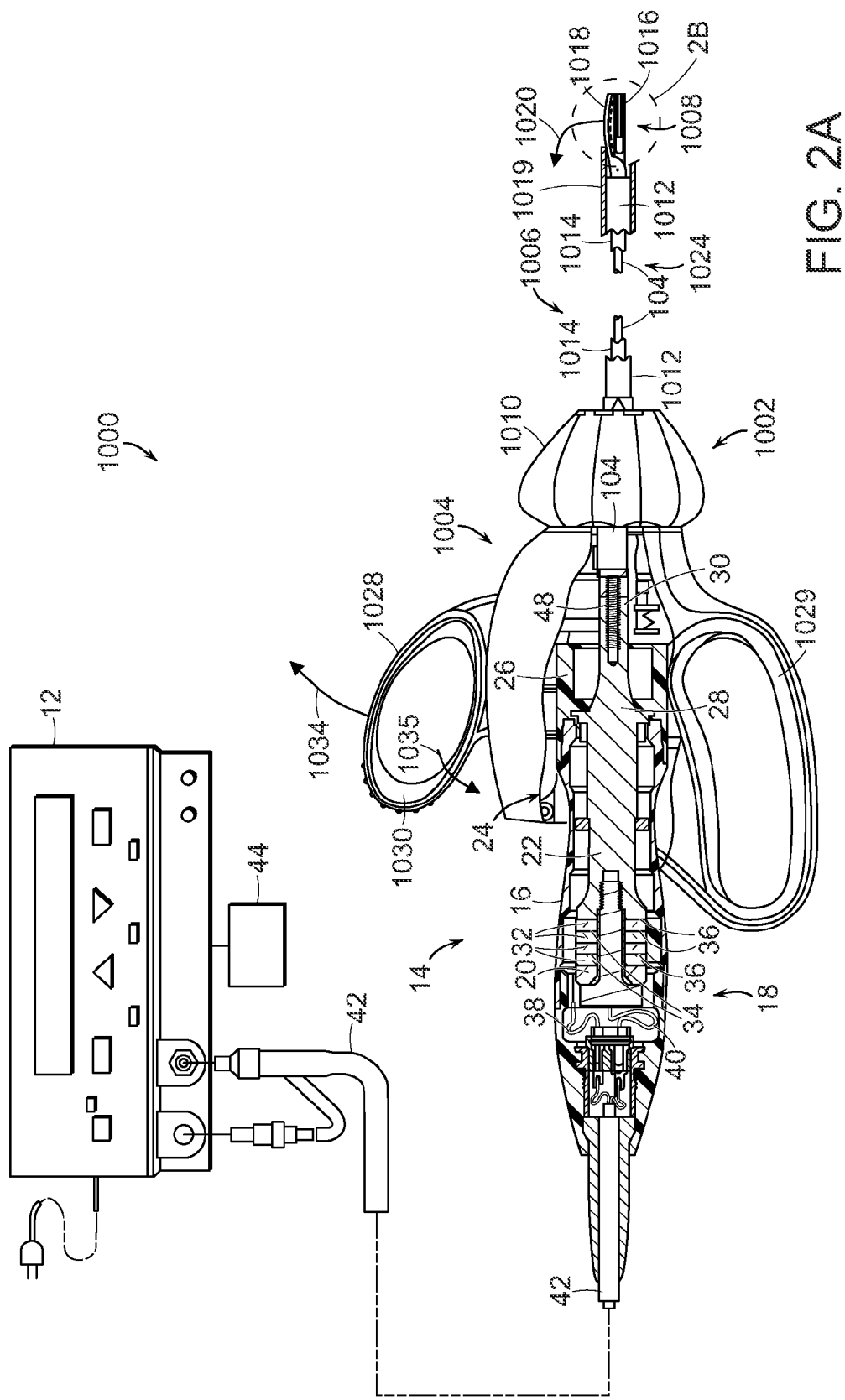

FIG. 2A illustrates one embodiment of an ultrasonic system 1000 comprising a multi-element end effector. One embodiment of the ultrasonic system 1000 comprises the ultrasonic generator 12 coupled to the ultrasonic transducer 14 previously described with reference to FIG. 1. The ultrasonic transducer 14 is coupled to clamping coagulating shears 1002 comprising an instrument housing 1004. The acoustic assembly 18 delivers energy to a multi-element end assembly 1008 comprising an ultrasonic end effector 1016 shown in the form of an ultrasonically actuable blade. In order for the acoustic assembly 18 to deliver energy to the end effector 1016 portion of the multi-element end assembly 1008, all components of the acoustic assembly 18 are acoustically coupled to the ultrasonically active portions of the clamping coagulating shears 1002. Accordingly, the distal end of the ultrasonic transducer 14 may be acoustically coupled via the surface 30 to the proximal end of the ultrasonic transmission waveguide 104 by way of the threaded connection stud 48.

As previously discussed with reference to the ultrasonic system 10 shown in FIG. 1, the components of the acoustic assembly 18 are preferably acoustically tuned such that the length of any assembly is an integral number of one-half wavelengths (nλ/2), where the wavelength λ is the wavelength of a pre-selected or operating longitudinal vibration drive frequency $f_d$ of the acoustic assembly 18. The acoustic assembly 18 may incorporate any suitable arrangement of acoustic elements.

The clamping coagulating shears 1002 may be preferably attached to and removed from the acoustic assembly 18 as a unit. The proximal end of the clamping coagulating shears 1002 preferably acoustically couples to the distal surface 30 of the acoustic assembly 18. The clamping coagulating shears 1002 may be coupled to the acoustic assembly 18 by any suitable means.

The clamping coagulating shears 1002 preferably includes an instrument housing 1004 and an elongated member 1006. The elongated member 1006 may be selectively rotated with respect to the instrument housing 1004 via the rotation knob 1010. The instrument housing 1004 includes a pivoting handle portion 1028 and a fixed handle portion 1029.

An indexing mechanism (not shown) is disposed within a cavity of the instrument housing 1004 and is preferably coupled or attached on an inner tube 1014 to translate movement of the pivoting handle portion 1028 to linear motion of the inner tube 1014 to open and close the multi-element end assembly 1008. The pivoting handle portion 1028 includes a thumb loop 1030. A pivot pin is disposed through a first hole of the pivoting handle portion 1028 to allow pivoting. As the thumb loop 1030 of the pivoting handle portion 1028 is moved in the direction of arrow 1034, away from the instrument housing 1004, the inner tube 1014 slides distally away from the proximal end to pivot the clamp arm 1018 of the multi-element end assembly 1008 into an open position in the direction indicated by arrow 1020. When the thumb loop 1030 of the pivoting handle portion 1028 is moved in the opposite direction toward the fixed handle portion 1029 in the direction indicated by arrow 1035, the indexing mechanism slides the inner tube 1014 proximally away from the distal end to pivot the clamp arm 1018 of the multi-element end assembly 1008 into a closed position, as shown.

The elongated member 1006 of the clamping coagulating shears 1002 extends from the instrument housing 1004. The elongated member 1006 preferably includes an outer member or outer tube 1012, an inner member or inner tube 1014, and a transmission component or ultrasonic transmission waveguide 104.

The multi-element end assembly 1008 includes a clamp arm 1018 (or clamp arm assembly) and the ultrasonic end effector 1016. The ultrasonic end effector 1016 comprises folded elements as described in more detail below in FIGS. 4-21. The ultrasonic blade 1016 may be symmetrical or asymmetrical. In one embodiment, the clamp arm 1018 may comprise a tissue pad. Accordingly, the clamp arm 1018 may be referred to as a clamp arm assembly, for example. The clamp arm 1018 may be configured to apply a compressive or biasing force to the tissue to achieve faster coagulation and cutting of the tissue. The clamp arm 1018 is pivotally mounted about a pivot pin (not shown) to rotate in the direction indicated by arrow 1020. The clamp arm 1018 may be configured to create a predetermined force distribution profile along the length (preferably along the active length) of the clamp arm 1018. In the illustrated embodiment, the clamp arm 1018 applies the predetermined force profile substantially over the entire active length of the end effector 1016. At a center region, the clamp arm 1018 may exert a minimum force at a point coinciding with an antinode of the end effector 1016. A normal force is applied to the end effector 1016 by a reciprocating outer compression tube 1019 at or near the center of the clamp arm 1018. From the center of the clamp arm 1018, (e.g., the point of minimum force exerted by the clamp arm 1018) the force exerted by the clamp arm 1018 increases from the center outwardly towards the proximal end and the distal end to either side of the center of the clamp arm 1018 towards the ends of the clamp arm 1018. In this manner, the clamp arm 1018 exerts a force distribution profile over the active length of the end effector 1016 that is ideally inversely proportional to the velocity amplitude displacement of the end effector 1016. The combination of the velocity of the end effector 1016 and the force exerted by the clamp arm 1018 determines the force profile along the active length of the end effector 1016.

Components of the ultrasonic surgical systems 10 and 1000 may be sterilized by methods known in the art such as, for example, gamma radiation sterilization, Ethelyne Oxide processes, autoclaving, soaking in sterilization liquid, or other known processes. In the embodiment illustrated in FIG. 1, the end effector 50 and the ultrasonic transmission waveguide 104 are illustrated as a single unit construction from a material suitable for transmission of ultrasonic energy as previously discussed (e.g., Ti6Al4V, Aluminum, Stainless Steel, or other known materials). Alternately, the end effector 50 may be separable (and of differing composition) from the ultrasonic transmission waveguide 104, and coupled by, for example, a stud, weld, glue, quick connect mechanism, or other known methods. In the embodiment illustrated in FIG. 2, the ultrasonic transmission assembly 1024 of the clamping coagulating shears 1002 includes the multi-element end assembly 1008 coupled to the ultrasonic transmission waveguide 104. The length of the ultrasonic transmission waveguide 104 may be substantially equal to an integral number of one-half system wavelengths (n$\lambda$/2), for example.

Figure 2B:
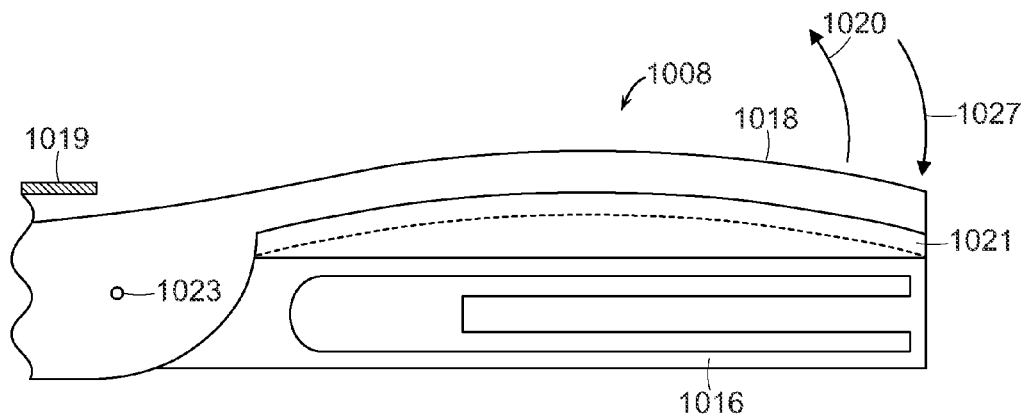

FIG. 2B illustrates one embodiment of the multi-element end assembly 1008. As illustrated, the multi-element end assembly 1008 comprises an arcuate clamp arm 1018 (or clamp arm assembly) and the ultrasonic and effector 1016. The ultrasonic end effector 1016 comprises folded elements as described in more detail below. The ultrasonic end effector 1016 may be symmetrical or asymmetrical. In one embodiment, a clamp arm assembly comprises the clamp arm 1018 with a tissue pad 1021. The clamp arm 1018 may be configured to apply a compressive or biasing force to tissue 1025 (FIGS. 2C, 2D) located between the tissue pad 1021 and the ultrasonic end effector 1016 to achieve faster coagulation and cutting of the tissue 1025. The compressive force may be applied by sliding the reciprocating outer compression tube 1019 over the clamp arm 1018. The clamp arm 1018 is pivotally mounted about a pivot 1023 to rotate open in the direction indicated by arrow 1020 and rotate closed in the direction indicated by arrow 1027. The clamp arm 1018 is configured to create a predetermined force distribution profile along the length of the clamp arm 1018 and the active length of the ultrasonic end effector 1016.

Figure 2C:
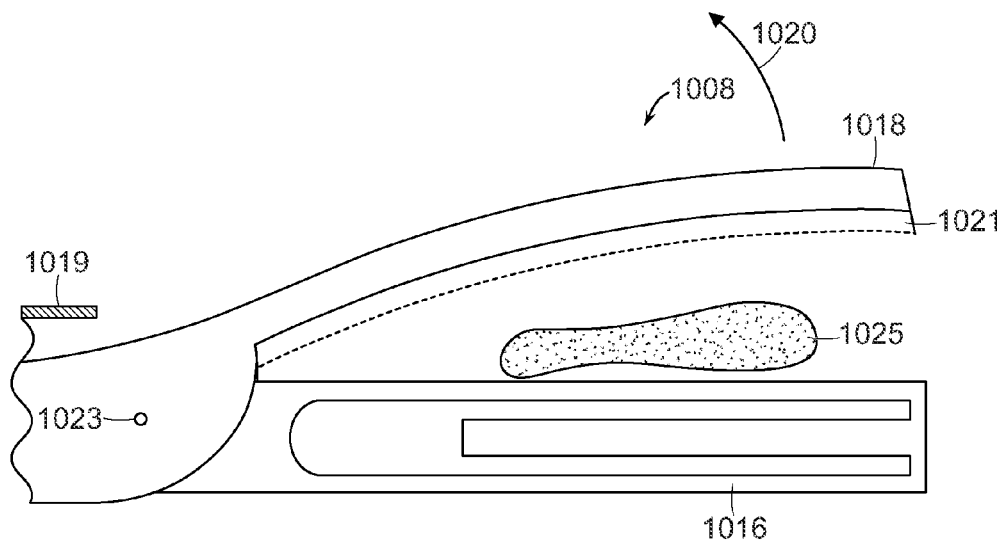
Figure 2D:
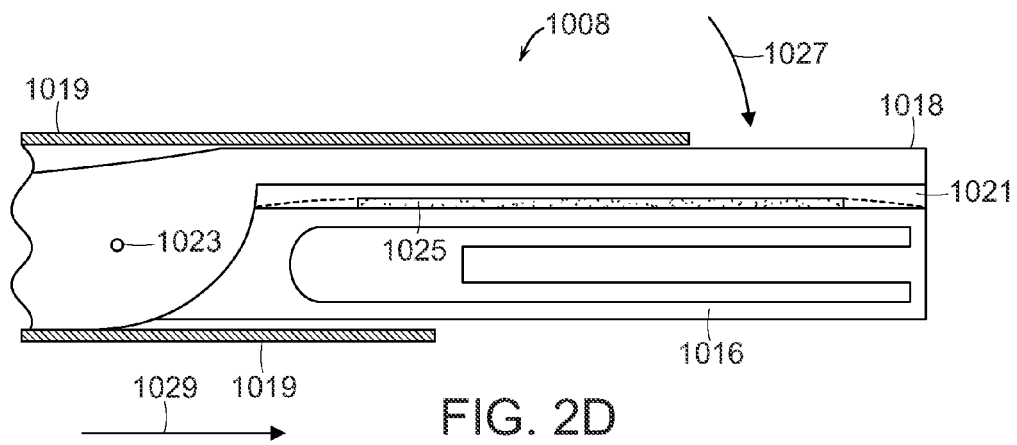

FIGS. 2C and 2D illustrate the clamp arm in various stages. FIG. 2C illustrates the clamp arm 1018 in an open position ready to receive the tissue 1025 between the tissue pad 1021 and the end effector 1016. The reciprocating outer compression tube 1019 is in a retracted position to enable the clamp arm 1018 to rotate in direction 1020 about the pivot 1023 to an open position. FIG. 2D illustrates the clamp arm 1018 rotated about the pivot 1023 to rotate in direction 1027 to a closed position with the reciprocating outer compression tube 1019 partially slid in direction 1029 over the clamp arm 1018 applying a partial compressive force over the clamp arm 1018. As illustrated in FIG. 2A, the reciprocating outer compression tube 1019 is located in a fully extended position to apply a full compressive force against the clamp arm 1018. Accordingly, the clamp arm 1018 applies a predetermined force distribution profile along the length of the clamp arm 1018 and the active length of the end effector 1016.

Figure 3:
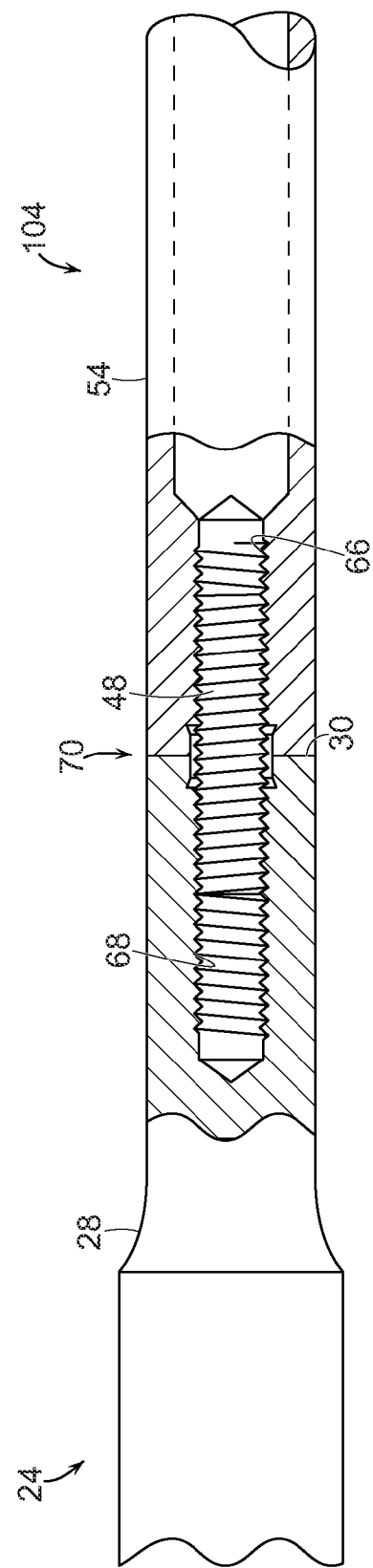
FIG. 3 illustrates one embodiment of a connection union/joint for an ultrasonic instrument.

FIG. 3 illustrates one embodiment of a connection union/joint 70 for an ultrasonic instrument. The connection union/joint 70 is located between the acoustic assembly 24 and an ultrasonic transmission component such as the ultrasonic transmission waveguide 104, for example. The connection union/joint 70 may be formed between an attachment post 54 of the ultrasonic transmission waveguide 104 and the surface 30 of the velocity transformer 28 located at the distal end of the acoustic assembly 24. The proximal end of the attachment post 54 comprises a female threaded substantially cylindrical recess 66 to receive a portion of the threaded stud 48 therein. The distal end of the velocity transformer 28 also may comprise a female threaded substantially cylindrical recess 68 to receive a portion of the threaded stud 48. The recesses 66 and 68 are substantially circumferentially and longitudinally aligned. In another embodiment (not shown), the stud may be formed as an integral component of the end of the ultrasonic transducer 14 shown in FIG. 1. For example, the threaded stud and the velocity transformer may be formed as a single unit construction with the stud projecting from a distal surface of the velocity transformer at the distal end of the acoustic assembly. In this embodiment, the stud is not a separate component and does not require a recess in the end of the transducer.

Those of ordinary skill in the art will understand that the various embodiments of the ultrasonic surgical instruments disclosed herein as well as any equivalent structures thereof could conceivably be effectively used in connection with other known ultrasonic surgical instruments without departing from the scope thereof. Thus, the protection afforded to the various ultrasonic surgical end effector embodiments disclosed herein should not be limited to use only in connection with the exemplary ultrasonic surgical instrument described above.

In the ensuing description, the letter "A" denotes the location of a displacement antinode and the letter "N" denotes the location of a displacement node. The distance between an antinode "A" and its nearest node "N" is one quarter wavelength ($\lambda$/4). One quarter wavelength ($\lambda$/4) is primarily determined by the frequency and speed of sound in the material. The speed of sound in most metals suitable for ultrasonic components is nominally 5,000 meters per second. Unless otherwise stated, in the embodiments described herein the wavelength is determined at an excitation frequency of 55.5 kHz where the wavelength is approximately 3.58 inches and one quarter wavelength ($\lambda$/4) is approximately 0.886 inches. For a waveguide formed of Ti6Al4V with a wave speed of 16,011 feet per second (4880 meters per second) the quarter wavelength is approximately 0.866 inches. Other materials that may lead to longer or shorter wavelengths may be employed. The active length in Ti6Al4V is nominally approximately 0.6 inches ($\approx$15 mm).

FIG. 4 is a schematic diagram of one embodiment of a hollow tubular end effector 400. FIG. 4A is a longitudinal cross-sectional view of the end effector 400. FIG. 4B is a cross-sectional view of the end effector 400 taken along line 4B-4B. A characteristic ultrasonic displacement curve 420 for the end effector 400 is graphically illustrated in FIG. 7 and is described in more detail below. With reference to FIGS. 4, 4A, and 4B, the end effector 400 comprises a body 406 having a proximal end 402, a distal end 404, and a cylindrical outer surface. The end effector 400 is described as a reference to facilitate understanding of the operation of the end effectors with folded elements in the embodiments shown in FIGS. 5 and 6. In the embodiment illustrated in FIG. 4, the end effector 400 has a physical length "L" of three quarter wavelengths (3$\lambda$/4). The end effector 400 may be formed of Ti6Al4V excited at a frequency of 55.5 kHz. Thus, one quarter wavelength ($\lambda$/4) is approximately 0.866 inches. Other materials that may provide longer or shorter wavelengths may be employed. The active length in Ti6Al4V is nominally approximately 0.6 inches ($\approx$15 mm).

In the illustrated embodiments, the proximal end 402 of the end effector 400 is located at the left side and the distal end 404 of the end effector 400 is located at the right side of the end effector 400. From left to right, the first quarter wavelength extends between the first node N1 and the first antinode A1; the second quarter wavelength extends between the first antinode A1 and the second node N2; and the third quarter wavelength extends between the second node N2 and the second antinode A2. The first node N1 is located at the proximal end 402 and the second antinode A2 is located at the distal end 404. It will be appreciated that in other embodiments, the end effector 400 may have a physical length that is an integer multiple of one quarter wavelength (n$\lambda$/4; where "n" is any positive integer; e.g., n=1, 2, 3 . . . ). The proximal end 402 of the end effector 400 is configured to couple to the velocity transformer 28 at the surface 30 as shown in FIGS. 1 and 2A. The proximal end 402 may be connected to or be a part of an additional transmission waveguide extending further in the proximal direction. For direct connection to the velocity transformer 28, the end effector 400 may be extended proximally by one quarter wavelength ($\lambda$/4) so that the proximal end 402 coincides with an antinode. Accordingly, the velocity transformer 28 and the end effector 400 may be joined together at their respective antinodes and the system frequency remains near the desired nominal value. In one embodiment, the nominal frequency is 55.5 kHz, for example. The added proximal quarter wavelength may have the same area as the outside parallel path (i.e., extended proximally by a quarter wave length). In which case, there is no gain. If the proximal segment has an increased area, then there will be amplitude gain due to the decrease in area relative to end effector 400 this represents. The end effector 400 may include gain, attenuation, and other features to achieve a desired performance as an ultrasonic surgical instrument operating at 55.5 kHz, for example. As shown in FIG. 4, the distal end 404 coincides with the second antinode A2 and, therefore, the distal end 404 is a point of maximum amplitude of the longitudinal ultrasonic vibration and the ultrasonic displacement is at a maximum. Conversely, the proximal end 402 coincides with the first node N1 and, therefore, the proximal end 402 is a point of minimum amplitude of the longitudinal ultrasonic vibration and the ultrasonic displacement is at a minimum.

Figure 5:
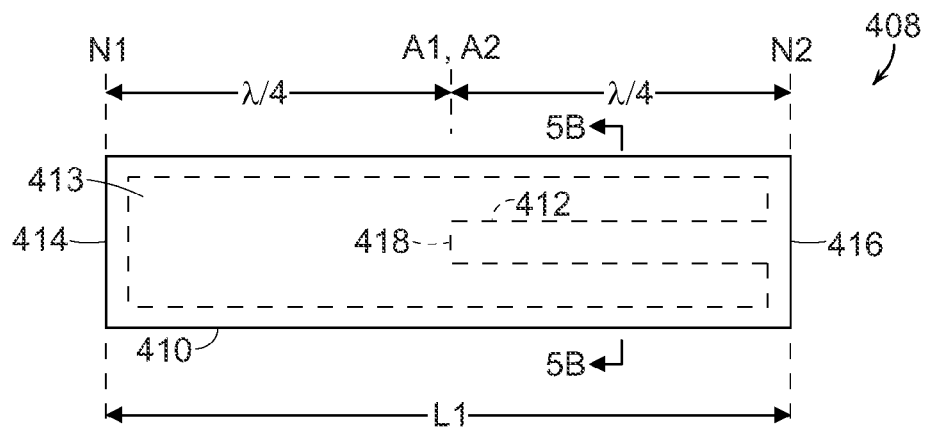
FIG. 5 is a schematic diagram of one embodiment of an end effector comprising a folded element defining a parallel acoustic path.
Figure 5A:
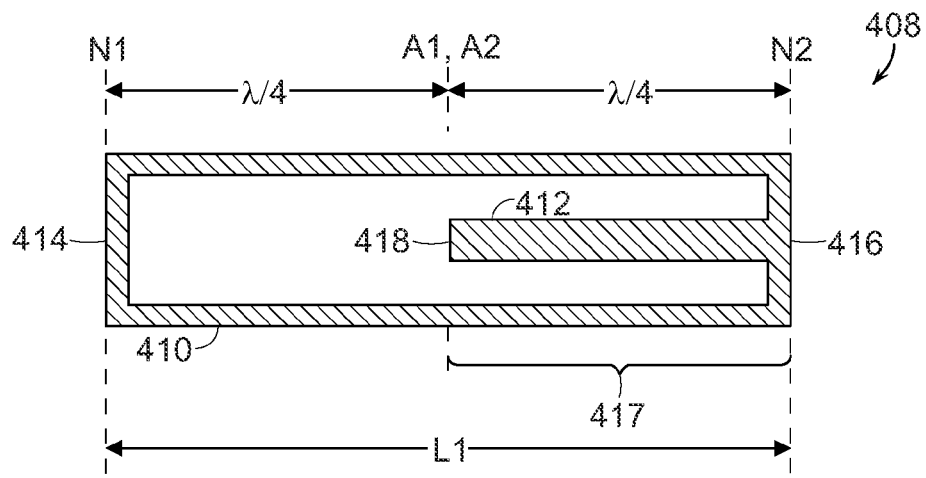
FIG. 5A is a longitudinal cross-sectional view of the end effector shown in FIG. 5.
Figure 5B:
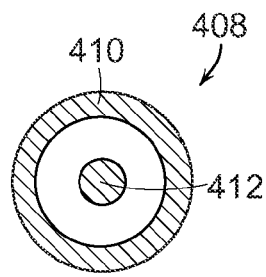
FIG. 5B is a cross-sectional view of the end effector shown in FIG. 5 taken along line 5B-5B.

FIG. 5 is a schematic diagram of one embodiment of an end effector 408 comprising a folded element 412 defining a parallel acoustic path. FIG. 5A is a longitudinal cross-sectional view of the end effector 408. FIG. 5B is a cross-sectional view of the end effector 408 taken along line 5B-5B. In one embodiment, the end effector 408 is suitable for use in the embodiment of the single-element end effector ultrasonic system 10 shown in FIG. 1. In another embodiment, the end effector 408 may be suitably adapted for use in the embodiment of the multi-element end effector system 1000 shown in FIG. 2A. A characteristic ultrasonic displacement curve 430 for the end effector 408 is graphically illustrated in FIG. 8 and is described in more detail below. The end effector 408 will now be described with reference to FIGS. 5, 5A, and 5B. The end effector 408 is a hollow tube ultrasonic transmission line comprising a body 410 having a proximal end 414 and a distal end 416 with a folded element 412 coupled to (e.g., folded at) the distal end 416 at the second node N2. The folded element 412 extends proximally from the second node N2 located at the distal end 416 towards the proximal end 414 into a hollow portion 413 of the end effector 408 to the first antinode A1. An acoustic distal end 418 of the folded element 412 terminates at the first antinode A1, where the first antinode A1 coincides with the second antinode A2. The first and second antinodes A1, A2 coincide when an end effector is folded at a node N and the length of the folded element is one quarter wavelength ($\lambda/4$). If the length of the folded element 412 is greater than or less than one quarter wavelength ($\lambda/4$), the first and second antinodes A1, A2 will not coincide. For example, if the fold is made between a node (N) and an antinode (A), the first and second antinodes A1, A2 will not coincide even if the length of the folded element 412 is one quarter wavelength ($\lambda/4$). These configurations are described herein below. In the illustrated embodiment, reference to the second antinode A2 is made merely to facilitate understanding the relation between the location of the fold and the length of the folded element 412. In the illustrated embodiment, the folded element 412 extends parallel to the longitudinal axis and to an outer surface of the body 410 of the end effector 408. The folded element 412 and the outer body of 410 of the end effector 408 define a parallel acoustic path 417 spanning the length of the folded element 412. In the illustrated embodiment, the parallel acoustic path 417 extends between the first antinode A1 and the second node N2. The end effector 408 in the illustrated embodiment has a physical length "L1" of two quarter wavelengths ($L1=2\lambda/4$). The folded element 412 is a solid rod. Over its length, the cross-sectional area of the folded element 412 is substantially equal to the longitudinal cross-sectional area of the end effector 408. The folded element 412 forms the distal quarter wavelength ($\lambda/4$) of the end effector 408. It will be appreciated that the physical length of the end effector 408 may be an integer multiple of one quarter wavelength ($n\lambda/4$; where "n" is any positive integer; e.g., n=1, 2, 3 ... ). Similarly, the folded element 412 may have a physical length that is an integer multiple of one quarter wavelength ($n\lambda/4$; where "n" is any positive integer; e.g., n=1, 2, 3 ... ). The embodiments are not limited in this context.

The proximal end 414 of the end effector 408 may be configured to couple to the velocity transformer 28 at the surface 30 as shown in FIGS. 1 and 2A. The proximal end 414 may be connected to or may form a portion of an ultrasonic transmission waveguide extending further in the proximal direction. For direct connection to the velocity transformer 28, the end effector 408 may be extended proximally by one quarter wavelength ($\lambda/4$) so that the proximal end 414 coincides with an antinode. Accordingly, the velocity transformer 28 and the end effector 408 may be joined together at their respective antinodes and the system frequency remains near the desired nominal value. In one embodiment, the nominal frequency is 55.5 kHz, for example. The added proximal quarter wavelength may have the same area as the outside parallel path (i.e., extended proximally by a quarter wave length). In which case, there is no gain. If the proximal segment has an increased area, then there will be amplitude gain due to the decrease in area with respect to 410 this represents. The end effector 408 may include gain, attenuation, and other features to achieve a desired performance as an ultrasonic surgical instrument operating at 55.5 kHz, for example. The end effector 408 comprises a free distal end 416 that coincides with the second node N2. The distal end 416 is a region of minimum amplitude displacement. The acoustic distal end 418 is located at a proximal end of the folded element 412. In the illustrated embodiment, the acoustic distal end 418 coincides with the first and second antinodes A1, A2 in terms of displacement. The acoustic distal end 418 is a region of maximum amplitude displacement. The external portion of the end effector 408 has a maximum displacement at its center located at the first antinode A1. Because the amplitude falls off symmetrically on either side of the first antinode A1, the active length is approximately 1.2 inches ($\approx$30 mm). This is double the active length of approximately 0.6 inches ($\approx$15 mm) of the end effector 400 illustrated in FIG. 4. In the end effector 400 the active length is measured from the second antinode A2 at the distal end 404 where the maximum amplitude displacement occurs to a point where the amplitude drops of to 50% of maximum somewhere between the second antinode A2 and the second node N2.

In other embodiments, the physical length of the folded element 412 may be greater than or less than one quarter wavelength ($\lambda/4$), or may be less than an integer multiple thereof ($n\lambda/4$), such that the ultrasonic amplitude displacement of the acoustic distal end 418 of the end effector 408 can be phased between maximum displacement and minimum displacement by suitably selecting the length of the folded element 412. In such embodiments, the length of the end effector 408 may be greater than or less than any number of quarter wavelengths ($\lambda/4$). It will be appreciated by those skilled in the art that in the various embodiments described herein, the length L1 of the end effector 408 is longer than the length of the folded segment 412. Nevertheless, the combined length of the end effector 408 and the folded element 412 may be any suitable number of quarter wavelengths ($\lambda/4$). In one embodiment, a particularly beneficial position for locating the fold is at in the region between the first antinode A1 and the second node N2 where the displacement amplitude drops off to 50% of maximum. Accordingly, the distal end 416 occurs at the limit of the active length. Moving towards the proximal end 414, the displacement amplitude remains above the minimum effective amplitude (>50% of maximum) to a region beyond the first antinode A1. Moving further towards the proximal end 414, the amplitude begins to drop below the desired 50% amplitude level. In this manner, the active length for end effectors designed with titanium (Ti) operating at 55.5 kHz may be extended to approximately 1.2 inches (≈30 mm).

At the location of the "fold", the longitudinal extension of the end effector 408 retains the ultrasonic displacement characteristics of that location without the fold. For example, in the embodiments illustrated in FIGS. 5, 5A, and 5B, the fold is located at the second node N2, at the distal end 416, and the folded element 412 extends proximally one quarter wavelength (λ/4) from the distal end 416 to the first and second antinodes A1, A2, which coincide with the acoustic distal end 418. The displacement pattern and locations of the first and second nodes N1, N2 remain the same along the longitudinal length of the end effector 408. The second node N2 remains a node, e.g., minimum or no displacement amplitude, even though it "presents" a free-end. Accordingly, the distal end 416 of the end effector 408 has substantially zero displacement and remains dull even when it is ultrasonically activated. This feature may be desirable in certain procedures to protect tissue that may come into contact with or may be in proximity to the distal end 416. Otherwise, an active distal end may create a surgical window or -otomy through the tissue it comes into contact with. Those skilled in the art will appreciate that the term "-otomy" refers to a combining form meaning "cutting, incision" of tissue or an organ, "excision" of an object, as specified by the initial element.

Figure 6:
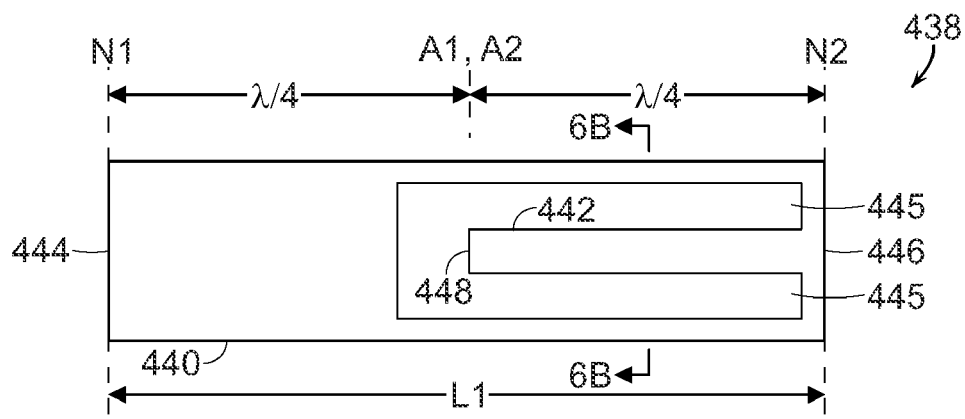
FIG. 6 illustrates a schematic diagram of one embodiment of an end effector comprising a folded element defining a parallel acoustic path.
Figure 6A:
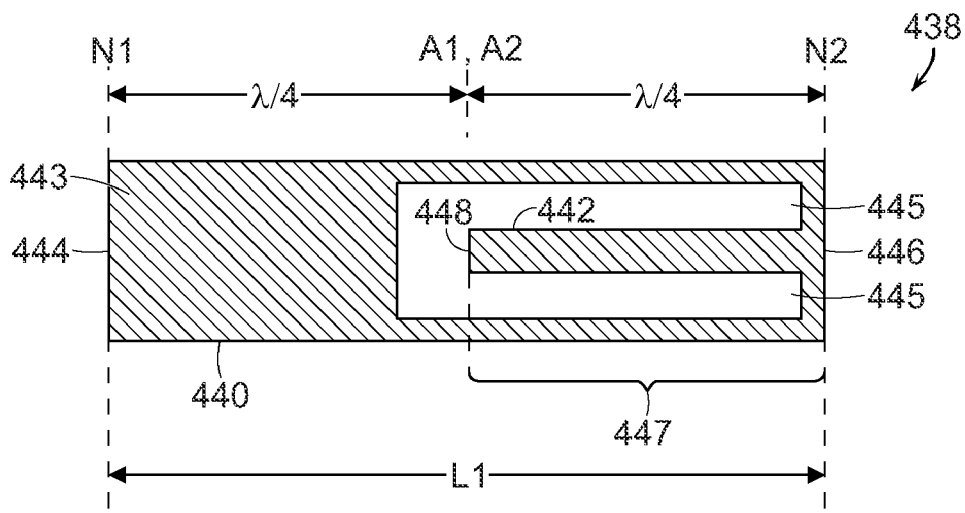
FIG. 6A is a longitudinal cross-sectional view of the end effector shown in FIG. 6.
Figure 6B:
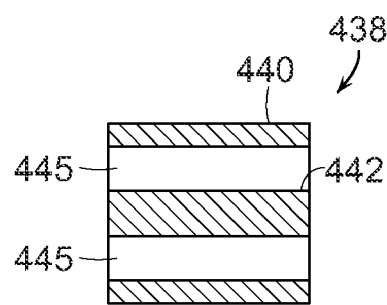
FIG. 6B is a cross-sectional view of the end effector shown in FIG. 6 taken along line 6B-6B.

FIG. 6 is a schematic diagram of one embodiment of an end effector 438 comprising a folded element 442 defining a parallel acoustic path. FIG. 6A is a longitudinal cross-sectional view of the end effector 438. FIG. 6B is a cross-sectional view of the end effector 438 taken along line 6B-6B. In one embodiment, the end effector 438 is suitable for use in the embodiment of the single-element end effector ultrasonic system 10 shown in FIG. 1. In another embodiment, the end effector 438 may be suitably adapted for use in the embodiment of the multi-element end effector system 1000 shown in FIG. 2A. The end effector 438 will now be described with reference to FIGS. 6, 6A, and 6B. The end effector 438 is a substantially solid ultrasonic transmission line comprising a body 440 having a proximal end 444 and a distal end 446 and the folded element 442 coupled to the distal end 446 at the second node N2. The end effector 438 comprises a slot 445 formed in a distal end of the solid portion 443 thereof. The folded element 442 extends proximally from the second node N2 located at the distal end 446 into the slot 445 parallel to the longitudinal axis towards the proximal end 444 to the first antinode A1. An acoustic distal end 448 of the folded element 442 terminates at the first antinode A1, where the first antinode A1 coincides with the second antinode A2. The first and second antinodes A1, A2 coincide when an end effector is folded at a node N and the length of the folded element is one quarter wavelength (λ/4). If the length of the folded element 442 is greater than or less than one quarter wavelength (λ/4), the first and second antinodes A1, A2 will not coincide. Also, if the fold is made between a node (N) and an antinode (A), the first and second antinodes A1, A2 will not coincide even if the length of the folded element 442 is one quarter wavelength (λ/4). These configurations are described herein below. In the illustrated embodiment, reference to the second antinode A2 is made merely to facilitate understanding the relationship between the location of the fold and the length of the folded element 442. In the illustrated embodiment, the folded element 442 extends parallel to the longitudinal axis and to an outer surface of the body 440 of the end effector 408. The folded element 442 and an external surface of the body 440 of the end effector 438 define a parallel acoustic path 447 spanning the length of the folded element 442. In the illustrated embodiment, parallel acoustic path 447 extends between the first antinode A1 and the second node N2. In the illustrated embodiment, the folded element 442 is configured as a rod of rectangular cross section extending in the slot 445 formed within the end effector 438. In the illustrated embodiment, the end effector 438 has a physical length "L1" of two quarter wavelengths (2λ/4). The folded element 442 may have a physical length of approximately one quarter wavelength (λ/4). Over its length, the longitudinal cross-sectional area of the folded element 442 is substantially equal to the longitudinal cross-sectional area of the end effector 438. It will be appreciated that the physical length of the folded transmission end effector 438 may be an integer multiple of one quarter wavelength (nλ/4; where "n" is any positive integer; e.g., n=1, 2, 3 . . . ). Similarly, the folded element 442 may have a physical length that is an integer multiple of one quarter wavelength (nλ/4; where "n" is any positive integer; e.g., n=1, 2, 3 . . . ). The embodiments are not limited in this context.

The proximal end 444 of the end effector 438 is configured to couple to the velocity transformer 28 at the surface 30 as shown in FIGS. 1 and 2A. The proximal end 444 may be connected to or may form a portion of an additional transmission waveguide extending further in the proximal direction. For direct connection to the velocity transformer 28, the end effector 438 may be extended proximally by one quarter wavelength (λ/4) so that the proximal end 444 coincides with an antinode. Accordingly, the velocity transformer 28 and the end effector 438 may be joined together at their respective antinodes and the system frequency remains near the desired nominal value. In one embodiment, the nominal frequency is 55.5 kHz, for example. The added proximal quarter wavelength may have the same area as the outside parallel path (i.e., extended proximally by a quarter wave length). In which case, there is no gain. If the proximal segment has an increased area, then there will be amplitude gain due to the decrease in area with respect to 438 this represents. The end effector 438 may include gain, attenuation, and other features to achieve a desired performance as an ultrasonic surgical instrument operating at 55.5 kHz, for example. The end effector 438 comprises a free distal end 446 that coincides with the second node N2. The distal end 446 is a region of minimum amplitude displacement. The acoustic distal end 448 is located at a proximal end of the folded element 442. In the illustrated embodiment, the acoustic distal end 448 coincides with the first and second antinodes A1, A2 in terms of displacement. The acoustic distal end 448 is a region of maximum amplitude displacement. The external portion of the end effector 438 has a maximum displacement at its center located at the first antinode A1. Because the amplitude falls off symmetrically on either side of the first antinode A1, the active length is approximately 1.2 inches (≈30 mm). This is double the active length of approximately 0.6 inches (≈15 mm) of the end effector 400 illustrated in FIG. 4.

In other embodiments, the physical length of the folded element 442 may be greater than or less than one quarter wavelength (λ/4), or maybe less than an integer multiple thereof (nλ/4), such that the ultrasonic displacement of the acoustic distal end 448 of the end effector 438 can be phased between maximum displacement and minimum displacement by suitably selecting the length of the folded element 442. In such embodiments, the length of the end effector 438 may be greater than or less than any number of quarter wavelengths ($\lambda/4$). It will be appreciated by those skilled in the art that in the various embodiments described herein, the length L1 of the end effector 438 is longer than the length of the folded element 442. Nevertheless, the combined length of the end effector 438 and the folded element 442 may be any suitable number of quarter wavelengths ($\lambda/4$). In one embodiment, a particularly beneficial position for locating the fold is at in the region between the first antinode A1 and the second node N2 where the displacement amplitude drops off to 50% of maximum. Accordingly, the distal end 446 occurs at the limit of the active length. Moving towards the proximal end 444, the displacement amplitude remains above the minimum effective amplitude (>50% of maximum) to a region beyond the first antinode A1. Moving further towards the proximal end 444, the amplitude begins to drop below the desired 50% amplitude level. In this manner, the active length for end effectors designed with titanium (Ti) operating at 55.5 kHz may be extended to approximately 1.2 inches ($\approx$30 mm).

At the location of the "fold", the longitudinal extension of the end effector 438 retains the ultrasonic displacement characteristics of that location without the fold. For example, in the embodiments illustrated in FIGS. 6, 6A, and 6B, the fold is located at the second node N2, at the distal end 446, and the folded element 442 extends proximally one quarter wavelength ($\lambda/4$) from the distal end 446 to the first and second antinodes A1, A2, which coincide with the acoustic distal end 448. The displacement pattern and locations of the first and second nodes N1, N2 remain the same along the longitudinal length of the end effector 438. The second node N2 remains a node, e.g., minimum or no displacement amplitude, N2 even though it "presents" a free-end. Accordingly, the distal end 446 of the end effector 438 has substantially zero displacement and remains dull even when it is ultrasonically active. This feature may be desirable in certain procedures to protect tissue that may come into contact with or may be in proximity to the distal end 446. Otherwise, an active distal end may create a surgical window or -otomy through the tissue it comes into contact with.

FIG. 7 graphically illustrates a characteristic ultrasonic displacement curve 420 for the end effector 400 shown in FIGS. 4, 4A, and 4B. The displacement curve 420 illustrates displacement in terms of ultrasonic amplitude along the vertical axis and quarter wavelengths ($\lambda/4$) along the horizontal axis. The ultrasonic amplitude of the displacement curve 420 is approximately zero at the proximal end 402, which is the location of the first node N1. The first antinode A1 is located one quarter wavelength ($\lambda/4$) from the proximal end 402. Moving distally along the end effector 400, the ultrasonic amplitude of the displacement curve 420 at the first (e.g., proximal) antinode A1 is $-1$ ($-100\%$), meaning that the first antinode A1 is a location of maximum or peak ultrasonic displacement. It is noted that the negative sign represents the phase of the ultrasonic displacement at the first antinode A1 relative to the second (e.g., distal) antinode A2. The displacement, however, may be characterized as temporal oscillations in accordance with equation (1) above. The second node N2 is located two quarter wavelengths ($2\lambda/4$) from the proximal end 402. Moving distally along the end effector 400, the ultrasonic amplitude of the displacement curve 420 at the second node N2 is zero. The second antinode A2 is located at the distal end 404, which is located at a distance of three quarter wavelengths ($3\lambda/4$) from the proximal end 402. Moving distally along the end effector 400, the amplitude of the displacement curve 420 at the second antinode A2 is $+1$ ($+100\%$), meaning that the second antinode A2 is a location of maximum or peak ultrasonic displacement. As previously discussed, the active length of an ultrasonic instrument generally may be defined as the distance from an active distal end of an end effector (where ultrasonic displacement is at a maximum) to a proximal location along the end effector where the ultrasonic displacement amplitude drops below a predetermined level, such as 50%, as approaching a node (where ultrasonic displacement is at a minimum) is approached. As shown in FIG. 7, the end effector 400 has an active length 422 that extends from the second antinode A2 located at the distal end 404 to a proximal location 424, where the ultrasonic displacement drops to $+0.5$ ($+50\%$), or one half-peak level. The proximal location 424 is located within the third quarter wavelength portion. For the displacement curve 420 shown in FIG. 7, the active length 422 is approximately 0.65 quarter wavelengths or approximately 0.6 inches (>15 mm).

FIG. 8 graphically illustrates an ultrasonic displacement curve 430 for the end effectors 408 and 438 shown in FIGS. 5, 5A, 5B, and FIGS. 6, 6A, 6B respectively. The displacement curve 430 illustrates displacement in terms of ultrasonic amplitude along the vertical axis and quarter wavelengths ($\lambda/4$) along the horizontal axis. The ultrasonic amplitude of the displacement curve 430 is approximately zero at the proximal end 414, which is the location of the first node N1. The first antinode A1 is located one quarter wavelength ($\lambda/4$) from the proximal end 414. Moving distally along the outer segments 410 and 440 of the end effectors 408, 438, the ultrasonic amplitude of the displacement curve 430 at the first (e.g., proximal) antinode A1 is $+1(+100\%)$, meaning that the first antinode A1 is a location of maximum or peak ultrasonic displacement. The second node N2 is located two quarter wavelengths ($2\lambda/4$) from the proximal end 414. Moving distally along the end effector 408, 438, the amplitude of the displacement curve 430 at the second (e.g., distal) node N2 also is approximately zero. As shown in FIG. 8, the end effector 408, 438 has an active length 432 defined as the distance from a proximal location 434a, where the ultrasonic displacement curve 430 crosses above an ultrasonic amplitude of $+0.5$ ($+50\%$), e.g., one half-peak level, to a distal location 434b, where the ultrasonic displacement curve 430 crosses below an ultrasonic amplitude of $+0.5$ ($+50\%$), e.g., one half-peak level. For the displacement curve 430 shown in FIG. 8, the active length 432 is approximately 1.3 quarter wavelengths or approximately 1.2 inches ($\approx$30 mm). The peak displacement of the ultrasonic displacement curve 430 occurs in the middle of the active length 432 at the antinode A1. It decreases to either side of the middle as the first and second end nodes N1, N2 are approached. By way of comparison, the active length of the end effector 408, 438 is thus approximately double that of the end effector 400 shown in FIG. 4.

FIG. 9 illustrates a schematic diagram of one embodiment of a multi-element end effector 450 comprising the folded element 412 defining a parallel acoustic path 417. The multi-element end effector 450 is suitable for use in the embodiment of the multi-element end effector ultrasonic system 1000 shown in FIG. 2A. The multi-element end effector 450 comprises the end effector 408 operatively coupled to a clamp arm 452. The clamp arm 452 may comprise a tissue pad 454.

The ultrasonic amplitude displacement profile of the active length region of the end effector 408 requires a predetermined force profile by the clamp arm 452. In conventional end effectors, the ultrasonic amplitude displacement decreases moving proximally from the antinode (A) towards the node (N). The active length is defined as the region between a node (N) and an antinode (A) where the ultrasonic displacement remains at or above 50% of the maximum ultrasonic displacement within the region. It has been shown that at least to a first order that the generation of heat follows a simple frictional law, which may be expressed formulaically according to equation (2) as follows:

$$\text{Heat} = \mu v N \quad (2)$$

where:

$\mu$=a coefficient of friction;

$v$=the root mean squared (rms) value of the ultrasonic velocity; and

N=normal force.

To compensate for decreasing amplitude, and hence decreased ultrasonic velocity, in region away from the distal end of the end effector, conventional clamp arm assemblies generate the highest pressure at a proximal end of the end effector near the location of a clamp arm pivot point. This is generally accomplished by hinging the clamp arm at or near a distal node (N). As the clamp arm closes, the clamping force is greatest near the pivot point or juncture formed between the clamp arm and the end effector. Such conventional clamping mechanism may be neither optimum nor suitable for the amplitude displacement profile graphically illustrated in FIG. 8. As shown in FIG. 8, the displacement curve 430 is maximum in a center region at the first antinode A1 and decreases symmetrically away from the centrally located antinode A1 towards the first and second nodes N1, N2 to either side of the antinode A1.

The clamp arm 452 may be configured to apply a force against the end effector 408 that is inversely proportional to the displacement curve 430 (FIG. 8) of the end effector 408. The force distribution profile produced by the clamp pad/arm 452 is the inverse of the amplitude curve so that the product of ultrasonic velocity of the end effector 408 and the force against it remains nominally constant over the active length region. In both concepts the normal force would be applied at the center of the clamp arm/pad. Accordingly, in one embodiment, the clamp arm 452 may be configured as a leaf-spring like mechanism to apply a normal force 456 at the first antinode A1 of the end effector 408, a normal force 457a at a proximal end of the end effector 408, and a normal force 457b at a distal end of the end effector 408. In the illustrated embodiment when the clamp mechanism is fully engaged, the normal force 456 applied at the first antinode A1 is less than the normal forces 457a, 457b applied at the respective proximal and distal ends of the end effector 408. In one embodiment, the clamp arm 452 may comprise a leaf spring mechanism in the form of a slender arc-shaped length of spring steel of rectangular cross-section. Those skilled in the art will appreciate that other clamp pad/arm mechanisms may be employed to create a near symmetric force distribution from a center point that decrease from the center and increase towards the ends.

FIG. 10 illustrates a schematic diagram of one embodiment of a multi-element end effector 460 comprising the folded element 412 defining a parallel acoustic path. The multi-element end effector 460 is suitable for use in the embodiment of the multi-element end effector ultrasonic system 1000 shown in FIG. 2A. The multi-element end effector 460 comprises the end effector 408 operatively coupled to a hinged clamp arm assembly 462. The hinged clamp arm assembly 462 comprises first and second tissue pad members 464a, b. The hinged clamp arm assembly 462 may comprise a hinge configuration in the form of a first member 462a and a second member 462b coupled at a pivot point 468. The first and second members 462a, b are adapted to receive the corresponding first and second tissue pad members 464a, b. A spring 470 applies a force to the hinged first and second clamp arm members 462a, b. The spring 470 may be a torsional spring, flat spring, or any other suitable type of spring known in the art. The hinge also may be a living hinge where there is a central segment that is thinned out relatively to the longer segments of the clamp arm on either side. Those skilled in the art will appreciate that living hinges are well known in the field of mechanical design.

In one embodiment, the hinged clamp arm assembly 462 may be configured as a hinge-like mechanism comprising a pivot point 468 to apply the greatest forces 467a, b at the ends of the active length region of the end effector 408 with sufficient force 466 at the center located at the first antinode A1. The forces 466 and 467a, b applied by the clamp arm 462 against the end effector 408 are ideally inversely proportional to the displacement curve 430 graphically illustrated in FIG. 8.

FIG. 11 illustrates a longitudinal cross-sectional view of one embodiment of an extendable tubular end effector 478. In one embodiment, the end effector 478 is suitable for use in the embodiment of the single-element end effector ultrasonic system 10 shown in FIG. 1. In another embodiment, the end effector 478 may be suitably adapted for use in the embodiment of the multi-element end effector system 1000. The end effector 478 comprises a body 480 having a proximal end 484 and a distal end 486 and a folded element 482 slideably coupled to the body 480. In the illustrated embodiment, the end effector 478 is a tubular end effector shown in the extended configuration. The folded element 482 is slideably moveable in the directions indicated by arrows 490a, b along the longitudinal axis. Once it is extended, the folded element 482 is locked in place to act as a suitable ultrasonic transmission element. To place the end effector 478 in the extended configuration the folded element 482 is extended in the direction indicated by arrow 490a by any suitable techniques. In the illustrated embodiment the folded element 482 is configured as a cylindrical element. The cylindrical folded element 482 may be slid forwardly toward the distal end. Several mechanisms may be employed to slide the folded element 482. In one embodiment, the folded element 482 may be configured with a male threaded portion at a proximal end to engage a matching female threaded portion formed in the distal end of the 478. Once the folded element 482 is located either in the retracted or extended configurations, the folded element 482 is "locked" into position with sufficient force for suitable transmission of the ultrasonic energy to either the distal end 488 in the extended configuration or the acoustic distal end 489 in the retracted configuration. Additional mechanisms may be included to slide an exterior sheath to protect the tissue from the vibration in the proximal two quarter wavelength segments and expose the tissue to the distal quarter wavelength. Likewise a mechanism may be provided to slide the symmetric clamp arm/pad assemblies 452, 462 (FIGS. 9, 10) distally to be used with only the distal quarter wavelength.

In the retracted configuration (shown in phantom), the extendable end effector 478 has a physical length L1 of two quarter wavelengths ($2\lambda/4$). In the extended configuration, the end effector 478 has a physical length of approximately two quarter wavelength ($2\lambda/4$) and the folded element 482 has a length L3 of approximately one quarter wavelength ($\lambda/4$). The folded element 482 forms the distal quarter wavelength ($\lambda/4$) of the end effector 478. In the extended configuration, the combined length of the end effector 478 and the folded element 482 has a physical length L2 of approximately three quarter wavelengths (3λ/4). The folded element 482 may be formed as a solid rod with approximately the same longitudinal cross-sectional area as the cross-sectional area of the tubular end effector 478 spanning the parallel acoustic path 487. It will be appreciated that the end effector 478 may have a physical length that is an integer multiple of one quarter wavelength (nλ/4; where "n" is any positive integer; e.g., n=1, 2, 3 . . . ). Similarly, the folded element 482 may have a physical length that is an integer multiple of one quarter wavelength (nλ/4; where "n" is any positive integer; e.g., n=1, 2, 3 . . . ). The embodiments are not limited in this context.

In the retracted configuration, shown in phantom, the distal end 486 coincides with the second node N2. Thus, in the retracted configuration, the free distal end 486 at the node N2 portion of the end effector 478 has nominally zero displacement and provides a dull surface to avoid damage to neighboring tissues when use the active length of 480.

In the extended configuration, the folded element 482 extends from the second node N2 to the second antinode A2. A distal end 488 of the folded element 482 is a region of maximum amplitude displacement coinciding with the second antinode A2. In the extended mode, the distal end 488 may be used to create a surgical window, -otomy, or back-cutting. The folded element 482 may be retracted in the direction indicated by arrow 490b by any suitable techniques. In the retracted configuration (shown in phantom), the folded element 482 is slideably located into a hollow portion 483 of the end effector 478. In the retracted configuration, the end effector 478 comprises an acoustic distal end 489 located at the first antinode A1 in terms of displacement and defines a parallel acoustic path 487 with an outer surface of the body 480 of the end effector 478. In the illustrated embodiment, the parallel acoustic path 487 extends between the first antinode A1 and the second node N2. The acoustic distal end 489 is a region of maximum amplitude displacement. Because the acoustic distal end 489 is located within the hollow portion 483, unintended contact with adjacent tissue at high amplitude is avoided.

In the extended configuration, the distal end 488 may be suitable for other surgical procedures such as creating surgical windows, -otomies, and/or back-cutting. During a back-cutting procedure, the surgeon may employ the distal end 488 active tip of the end effector 478 to divide tissues along planes.

The proximal end 484 of the extendable end effector 478 is configured to couple to the velocity transformer 28 at the surface 30 as shown in FIGS. 1 and 2A, for example. The proximal end 484 may be connected to or may form a portion of an additional transmission waveguide extending further in the proximal direction. For direct connection to the velocity transformer 28, the end effector 478 may be extended proximally by one quarter wavelength (λ/4) so that the proximal end 484 coincides with an antinode. Accordingly, the velocity transformer 28 and the end effector 478 may be joined together at their respective antinodes and the system frequency remains near the desired nominal value. In one embodiment, the nominal frequency is 55.5 kHz, for example. The added proximal quarter wavelength may have the same area as the outside parallel path (i.e., extended proximally by a quarter wave length). In which case, there is no gain. If the proximal segment has an increased area, then there will be amplitude gain due to the decrease in area with respect to 478 this represents. The end effector 478 may include gain, attenuation, and other features to achieve a desired performance. In the retracted configuration, the end effector 478 comprises a free distal end 486 that coincides at the second node N2 in terms of amplitude displacement. The distal end 486 is a region of minimum amplitude where the longitudinal ultrasonic vibration and the ultrasonic displacement is at a minimum. In the extended configuration, the extendable end effector 478 also comprises a distal end 488 located at a second antinode A2. The distal end 488 is therefore a region of maximum amplitude where the longitudinal ultrasonic vibration and the ultrasonic displacement is at a maximum. Accordingly, the distal end 488 of the folded element 482 may be employed to effect tissue.

In other embodiments, the folded element 482 may be folded at a displacement region located between a node "N" and an antinode "A" such that the ultrasonic displacement of the acoustic distal end 488 may be phased between maximum displacement and minimum displacement as shown below in FIG. 20. The length of the folded parallel path 707 shown in FIG. 20 is greater than a quarter wavelength (>λ/4).

Yet in other embodiments, the physical length of the folded element 482 may be less that one quarter wavelength (λ/4), or less than an integer multiple thereof (nλ/4), such that the ultrasonic displacement of the distal end 488 is phased between maximum displacement and minimum displacement when the folded element 482 is retracted. The combined length L2 of the end effector 478 and the extended folded element 482 may be any suitable number of wavelengths (λ).

As previously discussed with reference to FIGS. 5, 5A, 5B, at the location of the "fold" the extendable end effector 478 retains the ultrasonic displacement characteristics of that location without the fold. For example, as shown in FIG. 11, the fold is located at the second node N2 and the folded element 482 is extendable one quarter wavelength (λ/4) from the distal end 486 coinciding with the second node N2 to the extended distal end 488 coinciding with the second antinode A2. In the retracted configuration, the second node N2 remains the second node N2 and "presents" a free-end.

FIG. 12 illustrates a schematic diagram of one embodiment of a rotatable end effector 500. In one embodiment, the extendable end effector 500 is suitable for use in the embodiment of the single-element end effector ultrasonic system 10 shown in FIG. 1. In another embodiment, the end effector 500 may be suitably adapted for use in the embodiment of the multi-element end effector system 1000. The end effector 500 comprises a body 501 having a proximal end 504 and a distal end 506 and a folded element 502 rotatably coupled to the body 501. In the illustrated embodiment, the end effector 500 is a slotted rectangular bar that comprises a solid elongated element 512 and a slot 519 formed at the distal end. The folded element 502 is rotatably moveable about a pivot axis 510 at a distal end 506 of the elongated element 512. To locate the end effector 500 in the extended configuration the folded element 502 may be rotated outwardly about the axis 510 in the direction indicated by arrow 514a. In the extended configuration the folded element 502 extends from the second node N2 to the second antinode A2 and behaves as a conventional ultrasonic instrument with maximum ultrasonic displacement occurring at the distal end 508 coinciding with the second antinode A2. To locate the end effector 500 in the retracted configuration (shown in phantom) the folded element 502 may be rotated inwardly about the axis 510 in the direction indicated by arrow 514b. In the retracted configuration, the distal end 508 of the end effector 500 also behaves as the acoustic distal end 509 located at the first antinode A1 in terms of displacement and forms a parallel acoustic path 517 with an outer surface of the body 501 of the end effector 500. The distal end 508 is a region of maximum amplitude where the longitudinal ultrasonic vibration and the ultrasonic displacement is at a maximum. The distal end 508 of the folded element 502 may be configured to effect tissue. In one embodiment the pivot axis 510 may be implemented as a hinge mechanism.

FIG. 13 is a schematic diagram of a straight elongated end effector 520. In the illustrated embodiment, the length L4 of the end effector 520 is two quarter wavelengths ($2\lambda/4$). The end effector 520 extends from a proximal end 522 located at a first antinode A1, through a node N1, and ends at a second antinode A2 at the distal end 524. The ultrasonic displacement curve of the end effector 520 is graphically illustrated in FIG. 16.

FIG. 14 is a schematic diagram of one embodiment of an end effector 530 comprising a folded element defining a parallel acoustic path 533. In the illustrated embodiment, the end effector 530 may be formed by folding the straight elongated rod end effector 520 (FIG. 13) at the location of the node N1. Thus, in the illustrated embodiment, the end effector 530 comprises a first element 532 extending from the first antinode A1 to the node N1 and a folded second element 534 that is folded back towards the proximal end to define the parallel acoustic path 533. In the illustrated embodiment, the folded second element 534 may be substantially parallel with the first element 532 and extends from the node N1 to the second antinode A2. In other embodiments, the folded second element 534 may not be parallel with the first element 532. In other embodiments, the folded second element 534 may extend from the node N1 to beyond the second antinode A2. It will be appreciated that the length L5 of the end effector 530 may be an integer multiple of one quarter wavelength ($n\lambda/4$; where "n" is any positive integer; e.g., n=1, 2, 3 . . . ). Similarly, the length of the folded second element 534 may be an integer multiple of one quarter wavelength ($n\lambda/4$; where "n" is any positive integer; e.g., n=1, 2, 3 . . . ). The proximal end 536 may be adapted and configured to couple to the velocity transformer 28 at the surface 30 as shown in FIGS. 1 and 2A, for example. The length of the proximal end 536 may be extended by additional quarter wavelengths to allow the end effector 530 and the velocity transformer 30 to be joined at corresponding antinodes. The proximal end 536 may be connected to or may form a portion of an additional transmission waveguide extending further in the proximal direction. The end effector 530 comprises an acoustic distal end 538 that is substantially aligned with the second antinode A2 and is configured to effect tissue (e.g., cut and/or coagulate). As illustrated in FIG. 14, the first and second elements 532, 534 may be coupled by a substantially rigid third member 540. The displacement of the first and second elements 532, 534 is referenced to the proximal end 536 and the acoustic distal end 538. Then the displacement at x=0, e.g., where the first and second antinodes A1, A2 are aligned, of the first and second elements 532, 534 is substantially equal and opposite. Thus, the first and second elements 532, 534 have the same magnitude of ultrasonic displacement along their longitudinal lengths but in opposite directions. Accordingly, the physical length L5 of the end effector 530 is one half the length L4 of the elongated end effector 520 (FIG. 13). The ultrasonic displacement curve of the end effector 530 is graphically illustrated in FIG. 17.

FIG. 15 is a schematic diagram of one embodiment of an end effector 550 comprising a folded element 562 defining a parallel acoustic path 556. In the illustrated embodiment, the end effector 550 may be formed by folding a distal segment of the straight end effector 520 (FIG. 13) at the location coinciding with the node N1 to define a folded element 552 in the form of a hook. Thus, in the illustrated embodiment, the end effector 550 comprises an elongated portion 554 extending from a proximal end 558 to a first antinode A1 and a folded element 552 extending from the first antinode A1 to the node N1. The folded element 552 comprises a first element 560 extending from the first antinode A1 to the node N1 and a folded second element 562 that extends from the node N1 to the second antinode A2. The folded second element 562 is folded back towards the proximal end to form a parallel acoustic path 553. The folded second element 562 is substantially parallel with the first element 560. The length of the end effector 550 may be an integer multiple of one quarter wavelength ($n\lambda/4$; where "n" is any positive integer; e.g., n=1, 2, 3 . . . ). Similarly, the lengths of the elongated element 554 and the folded element 556 may be an integer multiple of one quarter wavelength ($n\lambda/4$; where "n" is any positive integer; e.g., n=1, 2, 3 . . . ). The end effector 550 comprises a proximal end 558 configured to couple to the velocity transformer 28 at the surface 30 as shown in FIGS. 1 and 2A. The proximal end 558 may be connected to or may form a portion of an additional transmission waveguide extending further in the proximal direction. The end effector 550 comprises an acoustic distal end 564 that is located substantially aligned with the second antinode A2 and is configured to effect tissue (e.g., cut and/or coagulate) located in an opening 566 defined between the first and second elements 560, 562. As illustrated in FIG. 15, the folded element 552 or hook may be formed by bending a distal segment of a straight elongated rod ultrasonic transmission waveguide. Those skilled in the art will recognize that the elongated portion 554 and/or the folded element 552 may incorporate balancing features to minimize transverse vibration in the proximal elongated portion 554. Examples of ultrasonic surgical instruments with balanced end effector features are disclosed in U.S. Pat. Nos. 6,283,981 and 6,328, 751 and are incorporated herein by reference in their entirety. If the displacement of each of the first and second elements 560, 562 is referenced at location x=0, where the first and second antinodes A1, A2 are aligned, the displacement of the first and second elements 560, 562 is substantially equal and opposite. Thus, the first and second elements 560, 562 have the same ultrasonic displacement magnitude along their longitudinal lengths but in opposite directions. Accordingly, the physical length of the folded element 552 of the end effector 550 has twice the displacement across the tissue and therefore twice the effective velocity and therefore greater heating.

In the embodiment illustrated in FIG. 15, tissue may be located in the opening 566 defined between the first and second elements 560, 562. The length of the opening 566 may be one quarter wavelength ($\lambda/4$) or may be any integer multiple "n" of one quarter wavelength (($n\lambda/2$; where "n" is any positive integer; e.g., n=1, 2, 3 . . . ). In operation, the folded element 552 may be pulled through a portion of tissue to continuously transect and coagulate the tissue. In one embodiment, the folded element 552 may be employed as a fixed blade such as for mesentery takedown, for example. In such an embodiment, the first element 560 and the second element 562 may be located at a predetermined angle relative to each other at a distal end 568. The angled feature may be suitable to increase the nip pressure as the tissue is forced towards the node N1 at the distal end 568 during a transecting and coagulating procedure. In another embodiment, the folded portion 552 may be employed as a shear. In such an embodiment, however, the relative ultrasonic displacement amplitudes of each of the first and second elements 560, 562 may be adjusted to minimize any deleterious effects that may arise if the first and second elements 560, 562 come into physical metal-to-metal contact. In another implementation of the shears embodiment, the first and second elements 560, 562 may be formed with a relatively thin coating (e.g., polymeric, metallic, or oxide) to eliminate or minimize the direct metal-to-metal contact between the first and second elements 560, 562. A mechanism may be coupled to the distal end 568 to apply a squeezing force to flex the first and second elements 560, 562 such that they act in a shearing mode. In such an implementation, the first and second elements 560, 562 may be configured as the individual jaws that may be closed during the transacting process while still transmitting ultrasonic energy.

FIG. 16 graphically illustrates a characteristic ultrasonic displacement curve 570 of the straight elongated end effector 520 shown in FIG. 13. Displacement in terms of ultrasonic amplitude is shown along the vertical axis and the number of quarter wavelengths is shown along the horizontal axis. The displacement curve 570 amplitude at the first antinode A1 is +1 (+100%), meaning that the first antinode A1 is a location of maximum or peak ultrasonic displacement. The displacement amplitude decreases approaching the node N1 and at the node N1, the displacement curve 570 amplitude is zero. The displacement curve 570 amplitude increases toward a negative maximum displacement approaching the second antinode A2 and at the second antinode A2 the amplitude of the displacement curve 570 is −1 (−100%), meaning that the antinode A2 is a location of a negative maximum or peak ultrasonic displacement. The first antinode A1 is located at zero quarter wavelengths or at the proximal end 522 (FIG. 13), the node N1 is located at one quarter wavelength ($\lambda/4$) from the proximal end 522, and the second antinode A2 is located at two quarter wavelengths ($2\lambda/4$) from the proximal end 522. The active length 572 of the end effector 520 is approximately 0.65 quarter wavelengths. The active length 574 from the second antinode A2 to the displacement curve 570 at the 50% negative also is about 0.65 quarter wavelengths.

FIG. 17 graphically illustrates a characteristic ultrasonic displacement curve 580 of one embodiment of the end effector 530 comprising a folded element defining a parallel acoustic path 533 shown in FIG. 14. The curve 580 also applies to the other folded end effector embodiments shown in FIGS. 4, 5, and 6 and starting at their respective A1 antinodes. Displacement in terms of ultrasonic amplitude is shown along the vertical axis and the number of quarter wavelengths is shown along the horizontal axis. The displacement curve 580 amplitude at the first antinode A1 is +1 (+100%), meaning that the first antinode A1 is a location of maximum or peak ultrasonic displacement. The displacement amplitude decreases approaching the node N1. The displacement amplitude at the node N1 is zero. The displacement curve 580 amplitude increases toward a negative maximum displacement approaching the second antinode A2 and at the second antinode A2 the amplitude of the displacement curve 580 is −1 (−100%), meaning that the first antinode A1 is a location of a negative maximum or peak ultrasonic displacement. The first and second antinodes A1, A2 are located at the proximal end 536 and the node N1 is located at one quarter wavelength ($\lambda/4$) from the proximal end 536. The active length of the end effector 530 remains a nominal 0.65 of a wavelength. Both segments, 582, 584, however, have active lengths that act on tissue captured therebetween. Their active lengths, however, have displacements moving in opposite directions so the velocity across the tissue is essentially doubled and therefore thermal energy delivered to the tissue is doubled.

FIG. 18 is a schematic diagram of one embodiment of an end effector 600 comprising a folded element 602 defining a parallel acoustic path 607. In the illustrated embodiment, the fold is located just prior to where the distal node N2 would be located. FIG. 18A is a cross-sectional view of the end effector 600 shown in FIG. 18 taken along line 18A-18A. In one embodiment, the end effector 600 is suitable for use in the embodiment of the single-element end effector ultrasonic system 10 shown in FIG. 1. In another embodiment, the end effector 600 may be suitably adapted for use in the embodiment of the multi-element end effector system 1000 shown in FIG. 2A. The end effector 600 comprises a body 609 having a proximal end 604 and a distal end 606 and a folded element 602 coupled to the body 609. With referred now to FIGS. 18 and 18A, in one embodiment, the folded element 602 originates at a displacement region N' located between a node "N" and an antinode "A" extends beyond a first antinode A1 and terminates at an acoustic distal end 608, which coincides with a second antinode A2. The ultrasonic displacement of the acoustic distal end 608 may be phased between maximum displacement and minimum displacement by suitably locating the acoustic distal end 608 at a predetermined distance from the distal end 606. The end effector 600 comprises a proximal end 604 and a distal end 606. The folded element 602 originates at the distal end 606, which coincides with the displacement region N' located between the first antinode A1 and the second node N2. In the illustrated embodiment, N' is located at a distance that is less than one quarter wavelength ($\lambda/4$) from the second node N2. The folded element 602 extends from the distal end 606 parallel to the longitudinal axis B proximally towards the proximal end 604 to a region beyond the first antinode A1 to a second (e.g., folded) antinode A2. An outer surface of the body 609 of the distal portion of the end effector 600 and the folded element 602 define a parallel acoustic path 607. It will be appreciated that the length of the parallel acoustic path 607 is substantially the same as the length of the folded element 602. The second antinode A2 is shown merely to illustrate the location of the acoustic distal end 608. In the illustrated embodiment, the length L' of the end effector 600 has a physical length, which is less than two quarter wavelengths (L'<$2\lambda/4$). In the illustrated embodiment, the length of the folded element 602 is greater than one quarter wavelength (>$\lambda/4$). The folded element 602 may be formed as a solid rod forming the distal quarter wavelength of the end effector 600. It will be appreciated that the length of the end effector 600 may be an integer multiple of one quarter wavelength ($n\lambda/4$; where "n" is any positive integer; e.g., n=1, 2, 3 . . . ). Similarly, the folded element 602 may have a physical length that is an integer multiple of one quarter wavelength ($n\lambda/4$; where "n" is any positive integer; e.g., n=1, 2, 3 . . . ).

The proximal end 604 of the end effector 600 may be adapted and configured to couple to the velocity transformer 28 at the surface 30 as shown in FIGS. 1 and 2A, for example. For direct connection to the velocity transformer 28, the end effector 600 may be extended proximally by one quarter wavelength ($\lambda/4$) so that the proximal end 604 coincides with an antinode. Accordingly, the velocity transformer 28 and the end effector 600 may be joined together at their respective antinodes and the system frequency remains near the desired nominal value. In one embodiment, the nominal frequency is 55.5 kHz, for example. The added proximal quarter wavelength may have the same area as the outside parallel path (i.e., extended proximally by a quarter wave length). In which case, there is no gain. If the proximal segment has an increased area, then there will be amplitude gain due to the decrease in area with respect to 600. The end effector 600 may include gain, attenuation, and other features to achieve a desired performance. The proximal end 604 may be connected to or may form a portion of an additional transmission waveguide extending further in the proximal direction. The end effector 600 may include gain, attenuation, and/or other features to achieve a desired performance. The distal end 606 of the end effector 600 is a region where the displacements of the external and the internal parallel acoustic paths are equal. In the illustrated embodiment, the fold at N' may be selected to coincide with a 50% amplitude point. At the distal tip 606 the slopes of the displacement curve (FIG. 19) are opposite. Accordingly, the stresses are equal and opposite and there is stress equilibrium. The acoustic distal end 608 is located at the second antinode A2 in terms of displacement and is referred to as the Folded Antinode A2 in FIG. 19. The acoustic distal end 608 is therefore a region at a local negative maximum amplitude where the ultrasonic displacement of the longitudinal ultrasonic vibration is near a negative maximum.

In various embodiments, the length of the folded element 602 may be greater than or less than one quarter wavelength ($\lambda/4$), or may be less than an integer multiple thereof ($n\lambda/4$), such that the ultrasonic displacement of the acoustic distal end 608 may be phased between maximum displacement and minimum displacement depending on the location of the acoustic distal end 608 and the overall length of the folded element 602. The length of the end effector 600 and the folded element 602 may be any suitable number of quarter wavelengths ($\lambda/4$). A particularly beneficial position for the fold (N') is at the 50% amplitude level between the first antinode A1 and the second node N2. This means that the distal end 606 will be at the limit of the active length at the minimum effective amplitude to produce desired tissue effects. The amplitude remains above the minimum effective amplitude proximally beyond the first antinode A1. Going further proximally towards the first node N1, the amplitude falls below the desired level of 50%. This means the active length ($L_A$ shown in FIG. 19) extends to the distal end back to 1.2 inches ($\approx$30 mm) for end effectors designed with titanium operating at 55.5 kHz.

The location of the "fold" at N' along the longitudinal extension of the end effector 600 retains the ultrasonic displacement characteristics of that location prior to the fold. For example, in FIG. 18, the fold in the end effector 600 is located at N' between the first antinode A1 and the second node N2 and the solid rod folded element 602 extends one quarter wavelength ($\lambda/4$) from the distal end 606 to the acoustic distal end 608 located at the second antinode A2 just beyond the first antinode A1. The solid rod folded element 602 has the same longitudinal cross-sectional area as the longitudinal cross-sectional area of the end effector 600 spanning between the fold N' and the second antinode A2. The displacement at the fold N' is positive for the external parallel acoustic path 607 as well as the internal parallel acoustic path. Therefore, the distal end 606 of the end effector 600 is active when it is ultrasonically activated. FIG. 19 graphically illustrates an ultrasonic displacement curve 630 of the end effector 600.

FIG. 19 graphically illustrates a characteristic ultrasonic displacement curve 630 of one embodiment of the end effector 600 shown in FIGS. 18 and 18A comprising the folded element 602 defining the parallel acoustic path 607. The ultrasonic amplitude is shown along the vertical axis and quarter wavelength is shown along the horizontal axis. The amplitude of the displacement curve 630 is approximately zero at the proximal end 604, which is the location of the first node N1. The amplitude of the displacement curve 630 at the first antinode A1 is +1 (+100%), meaning that the first antinode A1 is the location of maximum or peak ultrasonic displacement. The first antinode A1 is located one quarter wavelength from the proximal end 604. The amplitude of the displacement curve 630 at the second node N2 would be approximately zero. However, the end effector 600 is folded at the fold N' just prior to where the second node N2 would be located. The second node N2 would be located two quarter wavelengths ($2\lambda/4$) from the proximal end 604. Therefore, the amplitude of the displacement curve 630 at the fold N' is positive. In the embodiment illustrated in FIG. 19, the location of the fold N' is selected such that the amplitude at the fold N' is at 50% of maximum. The fold N' is located at less than one quarter wavelengths ($<\lambda/4$) from the previous antinode A1. As previously discussed, the active length $L_A$ of an ultrasonic instrument is generally defined as the distance from the distal end of the end effector (where ultrasonic displacement is at a maximum) to a proximal location along the end effector where ultrasonic displacement decreases below a predetermined level approaching a node (where ultrasonic displacement is at a minimum). The active length 632 (or $L_A$) of the end effector 600 is defined as the distance from a proximal location 634a along the external parallel acoustic path where the ultrasonic displacement crosses above the 50% or one half-peak level to a distal location 634b at the fold N' at the free distal end 606 where the ultrasonic displacement crosses below 50% or one half-peak level. For the displacement curve 630 shown in FIG. 19, the active length 632 is approximately 1.3 quarter wavelengths or approximately 1.2 inches ($\approx$30 mm). The peak displacement of the ultrasonic displacement curve 630 occurs at the antinode A1. It decreases to either side of the middle approaching the first node N1 and the fold N'. By way of comparison, the active length of the end effector 630 is thus approximately double that of the hollow tube end effector 400 shown in FIG. 4.

FIG. 20 illustrates one embodiment of a slotted end effector 700 comprising a folded element 702 defining a parallel acoustic path 707. In the illustrated embodiment, the fold is located just prior to the most distal node N2. FIG. 20A illustrates cross-sectional view of the slotted end effector 700 shown in FIG. 20 taken along line 20A-20A. In one embodiment, the end effector 700 is suitable for use in the embodiment of the single-element end effector ultrasonic system 10 shown in FIG. 1. In another embodiment, the end effector 700 may be suitably adapted for use in the embodiment of the multi-element end effector system 1000 shown in FIG. 2A. The end effector 700 comprises a body 709 having a proximal end 704 and a distal end 706 and a folded element 702 coupled to the body 709. With reference to FIGS. 20 and 20A, the folded element 702 originates at a displacement region fold N', extends proximally, and terminates at an acoustic distal end 708. Thus, the folded element 702 extends from the distal end 706 at the fold N' and extends parallel to the longitudinal axis B from the distal end 706 proximally towards the proximal end 704 past the first antinode A1 to a second (e.g., folded) antinode A2. The fold N' is located at a distance of less than one-quarter wavelength ($\lambda/4$) from the most distal antinode A1. The end effector 700 comprises a proximal end 704 and a distal end 706. An outer surface of the body 709 of the distal portion of the end effector 700 and the folded element 702 define a parallel acoustic path 707. The second antinode A2 is shown merely to illustrate the location of the second antinode A2. In the illustrated embodiment, the length L' of the end effector 700 is less than two quarter wavelengths (L'<$2\lambda/4$). The end effector 700 comprises a solid proximal portion 712 and a slotted portion 710 formed at the distal portion. The slotted portion 710 defines the folded element 702. The length of the folded element 702 is approximately one quarter wavelength ($\lambda/4$). The folded element 702 may be a solid rod with the same cross-sectional area as the total cross-sectional defined by portions 702a and 702b of the end effector 700. The folded element 702 forms the distal quarter wavelength ($\lambda/4$) of the end effector 700. It will be appreciated that the length of the end effector 700 may be an integer multiple of one quarter wavelength (nλ/4; where "n" is any positive integer; e.g., n=1, 2, 3 . . . ). Similarly, the length of the folded element 702 may be an integer multiple of one quarter wavelength (nλ/4; where "n" is any positive integer; e.g., n=1, 2, 3 . . . ).

The end effector 700 comprises a proximal end 704 that is configured to couple to the velocity transformer 28 at the surface 30 as shown in FIGS. 1 and 2A, for example. For direct connection to the velocity transformer 28, the end effector 700 may be extended proximally by one quarter wavelength (λ/4) so that the proximal end 704 coincides with an antinode. Accordingly, the velocity transformer 28 and the end effector 700 may be joined together at their respective antinodes and the system frequency remains near the desired nominal value. In one embodiment, the nominal frequency is 55.5 kHz, for example. The added proximal quarter wavelength may have the same area as the outside parallel path (i.e., extended proximally by a quarter wave length). In which case, there is no gain. If the proximal segment has an increased area, then there will be amplitude gain due to the decrease in area with respect to 700. The end effector 700 may include gain, attenuation, and other features to achieve a desired performance. The proximal end 704 may be connected to or may form a portion of an additional transmission waveguide extending further in the proximal direction. The distal end 706 of the end effector 700 is a region where the displacements of the external and the internal parallel acoustic paths are equal. The proximal end 704 may be connected to or may form a portion of an additional transmission waveguide extending further in the proximal direction. The folded end effector 700 may include gain, attenuation, and other features to achieve a desired performance of an ultrasonic surgical instrument. The end effector 700 comprises a free distal end 706, such as a blade tip, that coincides with the fold N', which is less than one-quarter wavelength (λ/4) distance from the most proximal antinode A1. The distal end 706 is therefore a region where the displacements of the external and the internal parallel acoustic paths are both positive. In embodiment, the fold N' may be selected to coincide with a 50% amplitude point. At the distal tip 706 the slopes of the displacement curve (similar to the displacement curve shown in FIG. 19) are opposite. Accordingly, the stresses are equal and opposite and there is stress equilibrium. The end effector 700 also comprises an acoustic distal end 708 located at the second antinode A2 in terms of displacement and is referred to as the Folded Antinode A2. The acoustic distal end 708 is therefore a region near a local negative maximum amplitude where the longitudinal ultrasonic vibration and the ultrasonic displacement is near a negative maximum.

In various embodiments, the length of the folded element 702 may be greater than or less than one quarter wavelength (λ/4), or less than an integer multiple thereof (nλ/4), such that the ultrasonic displacement of the acoustic distal end 708 may be phased between maximum displacement and minimum displacement based on the location of the acoustic distal end 708 and the length of the folded element 702. The length of the slotted portion 710 may be greater than or less than any number of quarter wavelengths (λ/4). Yet together, the total length of the end effector 700 and the folded element 702 may be any suitable number of quarter wavelengths. A particularly beneficial position for the fold is at the 50% amplitude level between the first antinode A1 and the second node N2 at the fold N'. This means that the distal end 706 will be at the limit of amplitude to produce desired tissue effects. The amplitude remains above the minimum effective amplitude proximally beyond the first antinode A1. Proximally approaching the first node N1, the amplitude falls below the desired level of 50%. This means the active length extends to the distal end back to 1.3 wavelengths or 1.2 inches (≈30 mm) for end effectors designed with titanium operating at 55.5 kHz.

The location of the fold N' along the longitudinal extension of the end effector 700 retains the ultrasonic displacement characteristics of that location prior to the fold. For example, in FIG. 20, the fold N' is located at less than one quarter wavelength (λ/4) from the first antinode A1. As shown in FIG. 19, the displacement at the fold N' is positive for the external parallel acoustic path 707 as well as the internal parallel acoustic path. Therefore, the distal end 706 of the instrument is active when it is ultrasonically activated.

Figure 21A:
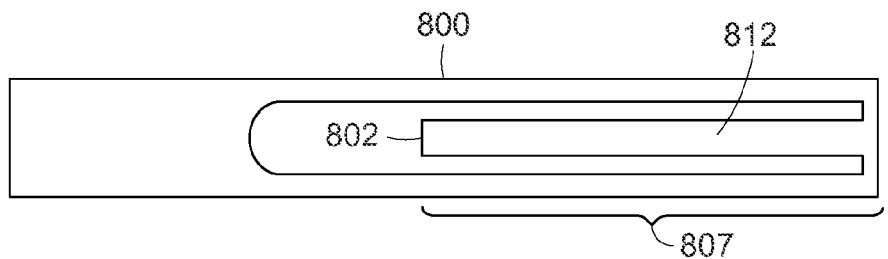

FIG. 21A illustrates one embodiment of a multi-element slotted end effector 800 comprising a folded element 812 defining a parallel acoustic path 807. The end effector 800 comprises a folded element 812 having an acoustic distal end 802. In the illustrated embodiment, the fold is located just prior to the most distal node. The fold N' is located at less than one quarter wavelengths (<λ/4) from the previous antinode, as described above with respect to FIGS. 19 and 20. The location of the fold N' is selected such that the amplitude at the fold N' is at 50% of maximum. The end effector 800 is suitable to form multiple seal zones in tissue clamped between a clamp pad assembly and sealing elements portions of the end effector 800.

Figure 21B:
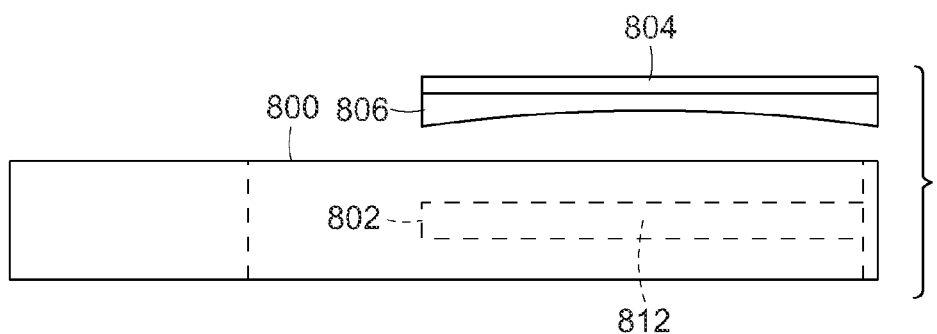

FIG. 21B illustrates schematically a side view of the end effector 800 operatively coupled to a clamp arm 804. The clamp arm 804 is adapted to receive a tissue pad 806. As previously described, the clamp arm 804/tissue pad 806 assembly (clamp arm assembly) may be configured to apply a compressive or biasing force to the tissue to achieve faster coagulation (e.g., sealing) and cutting of the tissue. The clamp arm 804 is pivotally mounted about a pivot pin (not shown) to rotate to an open position to receive tissue between the clamp arm 804 and the end effector 800. The clamp arm 804 and tissue pad 806 are configured to create a predetermined force distribution profile along the length (preferably along the active length of the end effector 800) of the clamp arm 804.

Figure 21C:
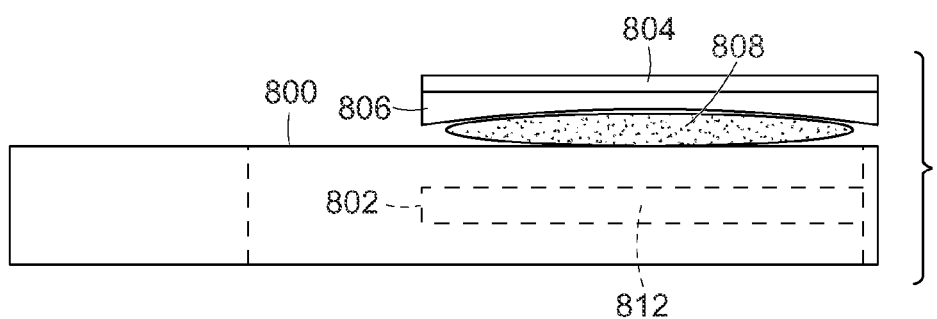

FIG. 21C illustrates schematically a side view of one embodiment of the end effector 800 operatively coupled to the clamp arm 804 with a section of tissue 808 located between the clamp arm 804 and the end effector 800. The tissue 808 is compressed between the clamp arm 804 and the end effector 800. The tissue 808 is sealed by activating the end effector 800 with ultrasonic energy.

Figure 21D:
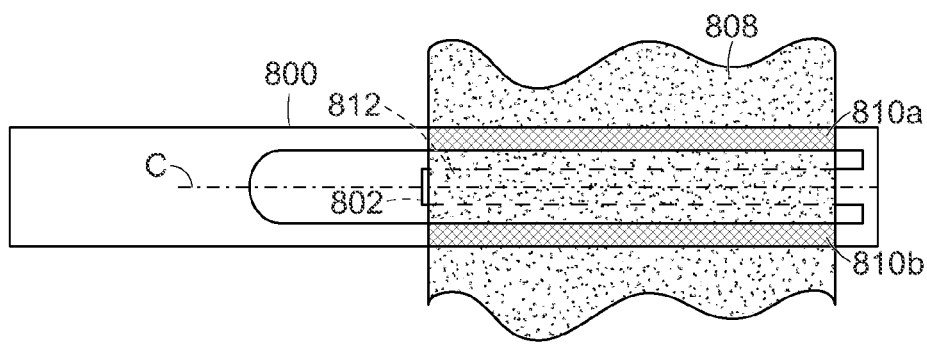

FIG. 21D illustrates schematically a top view of one embodiment of the end effector 800 with tissue sealing zones formed along sealing surfaces 810a and 810b of the end effector 800. In the embodiment illustrated in FIG. 21D, the clamp arm 804 is not shown for clarity. The tissue sealing zones are formed between the sealing elements 810a, 810b and the tissue pad 806. The width of the folded element 812 is selected such that the tissue 808 is compressed by the tissue pad 806 between the sealing edges 810a, 810b and the tissue pad 806 and is not compressed in the center portion between the sealing edges 810a, 810b. Once the tissue 808 is compressed between the sealing edges 810a, 810b and the tissue pad 806, the end effector 800 is ultrasonically energized to form tissue sealing zones along the sealing edges 810a, 810b. The heat energy generated by the end effector 800/tissue pad 806 combination is transferred to the tissue 808 along the sealing edges 810a, 810b leaving the center portion of the tissue 808 along a cut line C unsealed. Once the tissue sealing zones are formed along the sealing edges 810a, 810b, a knife may be used to cut the unsealed tissue 808 along cut line C.

The performance of the folded end effectors have been discussed in terms of the physics governing longitudinal plane wave propagation. Those skilled in the art will recognize that the presence of the fold will introduce shear stresses in the region of the fold. Therefore the nominal displacement at the free-end discussed in embodiments above represents an average value across the distal face of the end effector.

The incorporation of balance features has been discussed in reference to the end effector 550 of FIG. 15. Balance features can be incorporated in any portion of the folded end effectors as may be necessary to lessen the undesirable transverse motion.

It is to be understood that any of the embodiments of the ultrasonic transmission waveguides and/or end effectors described herein may be formed as tubular or solid members (e.g., rods, bars) with circular, rectangular, square, triangular, or other suitable polygonal cross-section. The ultrasonic transmission waveguides and/or end effectors may be formed with either straight or tapered edges to amplify, attenuate, or transmit the amplitude of the vibrations produced by the piezoelectric or magnetostrictive actuators. Furthermore, the folded elements may be formed as tubular or solid members (e.g., rods, bars) with circular, rectangular, square, triangular, or other suitable polygonal cross-section. The folded elements may be formed with either straight or tapered edges to amplify, attenuate, or transmit the amplitude of the vibrations produced by the piezoelectric or magnetostrictive actuators. The embodiments are not limited in this context.

With reference to any of the embodiments previously discussed, ultrasonic instruments may comprise two or more active ultrasonic end effectors to capture tissue between multiple active end effectors. For example, in one embodiment an instrument may comprise two active ultrasonic end effectors to capture tissue between two end effector elements with substantially equal and opposite ultrasonic displacement. In such embodiment, twice the power may be delivered to the tissue and the power may be symmetric with respect to the center of the tissue. This latter feature may improve seal strength and enable ultrasonic anastomoses. End effectors comprising folded elements as discussed above may be employed to achieve twice the active length. A folded element may exhibit ultrasonic displacement in a direct segment and opposite displacement in a parallel segment to achieve double active end effectors. A folded resonant element may be configured such that a distal segment is folded at a displacement node N. At the location of the fold, the distal end of the folded resonant element is a free end that remains a node N after it is folded. The acoustic distal end of the folded segment, however, is active and is located at an antinode A.

With reference to any of the embodiments previously discussed, it will be appreciated that in other embodiments, the folded element (e.g., folded rod ultrasonic end effector and the folded blade portion) may be coupled to a displacement region located between a node "N" and an antinode "A" such that the ultrasonic displacement of the acoustic elements may be phased between maximum displacement and minimum displacement. Yet in other embodiments, the physical length of the folded element may be less that one quarter wavelength ($\lambda/4$), or less than an integer multiple thereof ($n\lambda/4$), such that the ultrasonic displacement of the distal end is phased between maximum displacement and minimum displacement. In addition, the length of the straight portion of the folded ultrasonic transmission waveguide may be any suitable number of wavelengths ($\lambda$).

With reference to FIGS. 2A-D, 9, 10, and 21A-D that illustrate various embodiments comprising multi-element end effectors and clamp arm assemblies comprising proximal tissue pad segments, distal tissue pad segments, and tissue pad insert segments. The pivotal movement of the clamp arm assemblies with respect to the blades may be affected by the provision of a pair of pivot points on the clamp arm portion of the clamp arm assembly that interfaces with an ultrasonic surgical instrument via weld pin fastening or other fastening means (not shown). The tissue pad segments may be attached to the clamp arm by mechanical means including, for example, rivets, glues, adhesives, epoxies, press fitting or any other fastening techniques known in the art. Furthermore, the tissue pad segments may be removably attached to the clamp arm by any known techniques.

In various embodiments, the clamp arm may comprise a T-shaped slot for accepting a T-shaped flange of a tissue pad (e.g., the tissue pads 806, 1021 described herein). In various embodiments, a single unitary tissue pad assembly may comprise the tissue pad segment and further comprises a T-shaped flange for reception in a T-shaped slot in the clamp arm assembly. Additional configurations including dove tailed-shaped slots and wedge-shaped flanges are contemplated. As would be appreciated by those skilled in the art, flanges and corresponding slots have alternative shapes and sizes to removably secure the tissue pad to the clamp arm.

The devices disclosed herein can be designed to be disposed of after a single use, or they can be designed to be used multiple times. In either case, however, the devices can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam.

Although various embodiments have been described herein, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An end effector for use with an ultrasonic surgical instrument, comprising:
   a body extending along a longitudinal axis comprising a proximal end and a distal end, the body comprising an outer surface that defines an inner hollow portion, the proximal end of the body is configured to couple to an ultrasonic transducer configured to produce vibrations at a predetermined frequency and a predetermined amplitude; and
   a folded element having a predetermined length, the folded element comprising a first end coupled to the distal end of the body and extending proximally along the longitudinal axis from the distal end of the body toward the proximal end of the body into the hollow portion, the folded element comprising a second free acoustic end;
   wherein the folded element and the outer surface of the body define a single substantially parallel acoustic path spanning the length of the folded element, wherein the distal end of the body coincides with a node, wherein the node is a location of minimum amplitude displacement, wherein the second free acoustic end of the folded element coincides with an antinode, wherein the antinode is a location of maximum amplitude displacement, and wherein when the end effector is energized by the ultrasonic transducer, the distal end of the body coinciding with the node remains stable and the second free acoustic end vibrates at the predetermined frequency and amplitude.

2. The end effector of claim 1, wherein the body is configured as a tubular member and the folded element is configured as a solid member.

3. The end effector of claim 1, wherein the body comprises a solid portion at the proximal end and a hollow portion at the distal end, wherein the hollow portion defines a slot to receive the folded element therein.

4. The end effector of claim 1, wherein when the end effector is energized by the ultrasonic transducer, the outer surface of the body defines an active length that is greater than one quarter wavelength, wherein the active length is defined as a region that begins at the distal end of the body where amplitude displacement is at a minimum and extends proximally to a location where the amplitude displacement is one-half of a maximum amplitude displacement that occurs along the active length.

5. The end effector of claim 1, wherein the longitudinal cross-sectional area of the body is substantially equal to the longitudinal cross-sectional area of the folded element.

6. A surgical instrument, comprising:
   a transducer configured to produce vibrations along a longitudinal axis at a predetermined frequency and a predetermined amplitude;
   an ultrasonic end effector extending along the longitudinal axis coupled to the transducer, wherein the ultrasonic end effector comprises:
   a body extending along a longitudinal axis comprising a proximal end and a distal end, the body comprising an outer surface that defines an inner hollow portion, the proximal end of the body is configured to couple to an the ultrasonic transducer; and
   a folded element having a predetermined length, the folded element comprising a first end coupled to the distal end of the body and extending proximally along the longitudinal axis from the distal end of the body toward the proximal end of the body into the hollow portion, the folded element comprising a second free acoustic end;
   wherein the folded element and the outer surface of the body define a single substantially parallel acoustic path spanning the length of the folded element, wherein the distal end of the body coincides with a node, wherein the node is a location of minimum amplitude displacement, wherein the second free acoustic end of the folded element coincides with an antinode, wherein the antinode is a location of maximum amplitude displacement, and wherein when the end effector is energized by the ultrasonic transducer, the distal end of the body coinciding with the node remains stable and the second free acoustic end vibrates at the predetermined frequency and amplitude.

7. The surgical instrument of claim 6, wherein the body is configured as a tubular member and the folded element is configured as a solid member.

8. The surgical instrument of claim 6, wherein the body comprises a solid portion at the proximal end and a hollow portion at the distal end, wherein the hollow portion defines a slot to receive the folded element therein.

9. The surgical instrument of claim 6, wherein when the end effector is energized by the ultrasonic transducer, the outer surface of the body defines an active length that is greater than one quarter wavelength, wherein the active length is defined as a region that begins at the distal end of the body where amplitude displacement is at a minimum and extends proximally to a location where the amplitude displacement is one-half of a maximum amplitude displacement that occurs along the active length.

10. The surgical instrument of claim 6, wherein the longitudinal cross-sectional area of the body is substantially equal to the longitudinal cross-sectional area of the folded element.

11. An end effector for use with an ultrasonic surgical instrument, comprising:
    a body having an outer surface extending along a longitudinal axis comprising a proximal end and a distal end, the proximal end of the body is configured to couple to an ultrasonic transducer configured to produce vibrations at a predetermined frequency and amplitude; and
    a folded element having a predetermined length, the folded element comprising a first end coupled to the distal end of the body, the folded element extending proximally from the distal end of the body toward the proximal end of the body, the folded element comprising a second free acoustic end; and wherein the folded element and the outer surface of the body define a single substantially parallel acoustic path spanning the length of the folded element; and
    wherein when the end effector is energized by the ultrasonic transducer, the outer surface of the body defines an active length that is greater than one quarter wavelength, wherein the active length is defined as a region that begins at the distal end of the body where amplitude displacement is at a minimum and extends proximally to a location where the amplitude displacement is one-half of a maximum amplitude displacement that occurs along the active length.

12. The end effector of claim 11, wherein the body is configured as a tubular member and the folded element is configured as a solid member.

13. The end effector of claim 11, wherein the body comprises a solid portion at the proximal end and a hollow portion at the distal end, wherein the hollow portion defines a slot to receive the folded element therein.

14. The end effector of claim 11, wherein the distal end of the body is located in proximity to a node; and wherein the acoustic distal end of the folded element is located in proximity to an antinode.

15. The end effector of claim 11, wherein the distal end of the body substantially coincides with a first displacement region located between a node and an antinode; and wherein the acoustic distal end of the folded element substantially coincides with a second displacement region located between a node and an antinode.

16. The end effector of claim 11, wherein the longitudinal cross-sectional area of the body is substantially equal to the longitudinal cross-sectional area of the folded element.

17. The end effector of claim 11, wherein the distal end of the body coincides with a node, wherein the node is a location of minimum amplitude displacement, wherein the second free acoustic end of the folded element coincides with an antinode, wherein the antinode is a location of maximum amplitude displacement, and wherein when the end effector is energized by the ultrasonic transducer, the distal end of the body coinciding with the node remains stable and the second free acoustic end vibrates at the predetermined frequency and amplitude.

* * * * *